United States Patent
Machii et al.

(10) Patent No.: US 10,024,943 B2
(45) Date of Patent: Jul. 17, 2018

(54) MAGNETIC RESONANCE IMAGING APPARATUS AND MAGNETIC RESONANCE IMAGING METHOD

(71) Applicant: TOSHIBA MEDICAL SYSTEMS CORPORATION, Otawara-Shi, Tochigi-Ken (JP)

(72) Inventors: Yutaka Machii, Tochigi (JP); Hiroshi Kusahara, Tochigi (JP); Yoshimori Kassai, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 286 days.

(21) Appl. No.: 14/968,332

(22) Filed: Dec. 14, 2015

(65) Prior Publication Data

US 2016/0109546 A1    Apr. 21, 2016

Related U.S. Application Data

(63) Continuation of application No. PCT/JP2014/064828, filed on Jun. 4, 2014.

(30) Foreign Application Priority Data

Jun. 14, 2013  (JP) .................. 2013-125572

(51) Int. Cl.
*G01R 33/561* (2006.01)
*A61B 5/055* (2006.01)
(Continued)

(52) U.S. Cl.
CPC ........... *G01R 33/561* (2013.01); *A61B 5/055* (2013.01); *G01R 33/34* (2013.01); *G01R 33/385* (2013.01);
(Continued)

(58) Field of Classification Search
USPC ......................... 324/307, 310, 322; 382/131
See application file for complete search history.

(56) References Cited

U.S. PATENT DOCUMENTS

2010/0272337 A1* 10/2010 Shirai .................. G01R 33/485
382/131

FOREIGN PATENT DOCUMENTS

| JP | 2001-149342 | 6/2001 |
|---|---|---|
| JP | 2012-55684 | 3/2012 |
| JP | 2013-17811 | 1/2013 |

OTHER PUBLICATIONS

English Translation of International Preliminary Report on Patentability dated Dec. 15, 2015 for Application No. PCT/JP2014/064828.

(Continued)

*Primary Examiner* — Vincent Q Nguyen
(74) *Attorney, Agent, or Firm* — Nixon & Vanderhye P.C.

(57) ABSTRACT

According to one embodiment, an MRI apparatus includes a gradient coil, an RF coil, an RF receiver, and processing circuitry which controls these components to perform each pulse sequence. The processing circuitry sets a main-scan pulse sequence, a first pulse sequence which includes application of a gradient magnetic field in a readout direction, and a second pulse sequence which includes application of the gradient magnetic field in a readout direction, and whose acquisition region is shifted from the first pulse sequence. The processing circuitry reconstructs image data of the main scan, based on magnetic resonance signals acquired by the main-scan pulse sequence and phase difference data in the readout direction between first k-space data generated from the magnetic resonance signals acquired by the first pulse sequence and second k-space data generated from the magnetic resonance signals acquired by the second pulse sequence.

18 Claims, 9 Drawing Sheets

(51) Int. Cl.
*G01R 33/565* (2006.01)
*G01R 33/34* (2006.01)
*G01R 33/385* (2006.01)
*G01R 33/48* (2006.01)

(52) U.S. Cl.
CPC .... *G01R 33/56554* (2013.01); *G01R 33/4818* (2013.01); *G01R 33/5616* (2013.01); *G01R 33/5618* (2013.01); *G01R 33/56572* (2013.01)

(56) References Cited

OTHER PUBLICATIONS

International Search Report PCT/JP2014/064828, dated Jul. 1, 2014, 3 pages.

* cited by examiner

MAGNETIC RESONANCE IMAGING APPARATUS AND MAGNETIC RESONANCE IMAGING METHOD

CROSS-REFERENCE TO RELATED APPLICATIONS

This application is a continuation Application of No. PCT/JP2014/64828, filed on Jun. 4, 2014, and the PCT application is based upon and claims the benefit of priority from Japanese Patent Application No. 2013-125572, filed on Jun. 14, 2013, the entire contents of which are incorporated herein by reference.

FIELD

Embodiments described herein relate generally to a magnetic resonance imaging apparatus.

BACKGROUND

MRI is an imaging method which magnetically excites nuclear spin of an object (a patient) placed in a static magnetic field with an RF pulse having the Larmor frequency and reconstructs an image on the basis of MR signals generated due to the excitation. The above-described MRI means magnetic resonance imaging, the RF pulse means a radio frequency pulse, and the MR signal means a nuclear magnetic resonance signal.

In MRI, EPI (Echo Planar Imaging) is known an as a high speed imaging technique. In EPI, a scan is performed in such a manner that the gradient magnetic field in the readout direction is consecutively inverted at high speed for each nuclear magnetic excitation to cause consecutive echoes (MR signals).

More specifically, in EPI, all the data required for image reconstruction are acquired by generating consecutive gradient echoes while changing phase encode amount in order, after applying an excitation pulse and before the magnetization in the X-Y plane attenuates and disappears because of transverse relaxation.

There are some types of EPI such as EPI of spin echo type which is based on an SE (Spin Echo) technique and acquires a spin echo signal occurring subsequent to an excitation pulse and a refocusing pulse, EPI of an FE (Field Echo) type which is based on an FE technique and acquires an echo signal occurring subsequent to an excitation pulse, and EPI of an FFE (Fast FE) type which is based on a fast FE technique.

In addition, a type of EPI which reconstructs one image by combining data of echo trains obtained by applying plural excitation pulses is referred to as multi-shot EPI, whereas a type of EPI which reconstructs one image by application of one excitation pulse is referred to as SS (single-shot) EPI.

The pulse waveform of the gradient magnetic field in the readout direction in EPI has shorter pulse width and shorter pulse cycle length, as compared with other imaging techniques. In other words, the frequency component of the pulse waveform of the gradient magnetic field in the readout direction in EPI is high, as compared with other imaging techniques.

Meanwhile, a gradient magnetic field pulse is generated by applying a pulse electric current to a gradient coil. A waveform of the pulsed electric current applied to a gradient coil is ideally a block pulse, but actually becomes a trapezoidal wave having a rising edge region and a falling edge region. As a result, a pulse waveform of a gradient magnetic field does not become an ideal block pulse, but becomes a trapezoidal wave having a rising edge region and a falling edge region.

Generally, in high speed imaging techniques such as EPI, pulse width of a gradient magnetic field pulse is short, and a ratio of a rising edge region and a falling edge region in both ends of a pulse to the entire pulse width becomes high. Therefore, it is proposed to use sampled data over the entire pulse width for image reconstruction by sampling data in a rising edge region and a falling edge region as well as sampling data in a flat region of a pulse.

The method of sampling data in a rising edge region and a falling edge region is called Ramp Sampling. The Ramp Sampling gives a shorter data acquisition time, as compared with other methods of sampling data only in a period during which gradient magnetic field intensity is constant.

However, the raw data of MR signals sampled at regular time intervals in a rising edge region and a falling edge region do not become equally-spaced in a k-space, because these MR signals are sampled while the gradient magnetic field in the readout direction is changing. Thus, it is preferable to rearrange the sampled raw data of MR signals before image reconstruction, in such a manner that the sampled raw data become equally-spaced in the k-space. This rearrangement processing is generally called regridding.

In the conventional regridding processing, a waveform of a gradient magnetic field pulse is calculated based on an equivalent circuit model. This equivalent circuit model is close to an actual gradient magnetic field generation system, because skin effect and eddy currents are considered. Then, improvement in accuracy of regridding processing by performing regridding processing based on the waveform of the gradient magnetic field calculated in the equivalent circuit is achieved.

Although the above conventional regridding processing has satisfactory working effects, it is preferable to perform regridding processing as accurately as possible, in order to improve image quality.

Therefore, in MRI, novel technology to perform regridding processing more accurately than conventional technology has been desired.

DETAILED DESCRIPTION

According to one embodiment, an MRI apparatus includes: a gradient coil configured to apply a gradient magnetic field in accordance with a pulse sequence; an RF coil configured to transmit RF pulses causing nuclear magnetic resonance and receive nuclear magnetic resonance signals in accordance with the pulse sequence; an RF receiver configured to acquire the nuclear magnetic resonance signals received by the RF coil in accordance with the pulse sequence; and processing circuitry configured to control the gradient coil, the RF coil, and the RF receiver to perform a first pulse sequence, a second pulse sequence, and a main-scan pulse sequence.

The processing circuitry is configured to (a) set the first pulse sequence in which application of a gradient magnetic field in a readout direction is included, in such a manner that the nuclear magnetic resonance signals are acquired from a first acquisition region including at least a part of an imaging region of a main scan, (b) set the second pulse sequence in which application of the gradient magnetic field in the readout direction is included, in such a manner that the nuclear magnetic resonance signals are acquired from a second acquisition region including at least a part of the imaging region and being shifted from the first acquisition region are acquired, (c) set the main-scan pulse sequence in which application of the gradient magnetic field in the readout direction and a gradient magnetic field in a phase encode direction is included, in such a manner that the nuclear magnetic resonance signals from the imaging region are acquired, (d) generate first k-space data including a plurality of matrix elements, by sampling the nuclear magnetic resonance signals acquired by the first pulse sequence, (e) generate second k-space data including a plurality of matrix elements, by sampling the nuclear magnetic resonance signals acquired by the second pulse sequence, (f) calculate phase difference data indicative of phase difference in the readout direction between the first k-space data and the second k-space data, (g) generate main scan k-space data based on the nuclear magnetic resonance signals acquired by the main-scan pulse sequence and the phase difference data, and (h) reconstruct image data of the imaging region based on the main scan k-space data.

An MRI apparatus and an MRI method according to embodiments of the present invention will be described with reference to the accompanying drawings. Note that the same reference numbers are given for identical components in each figure, and duplicate explanation is omitted.

Configuration of the Present Embodiment

Figure 1:
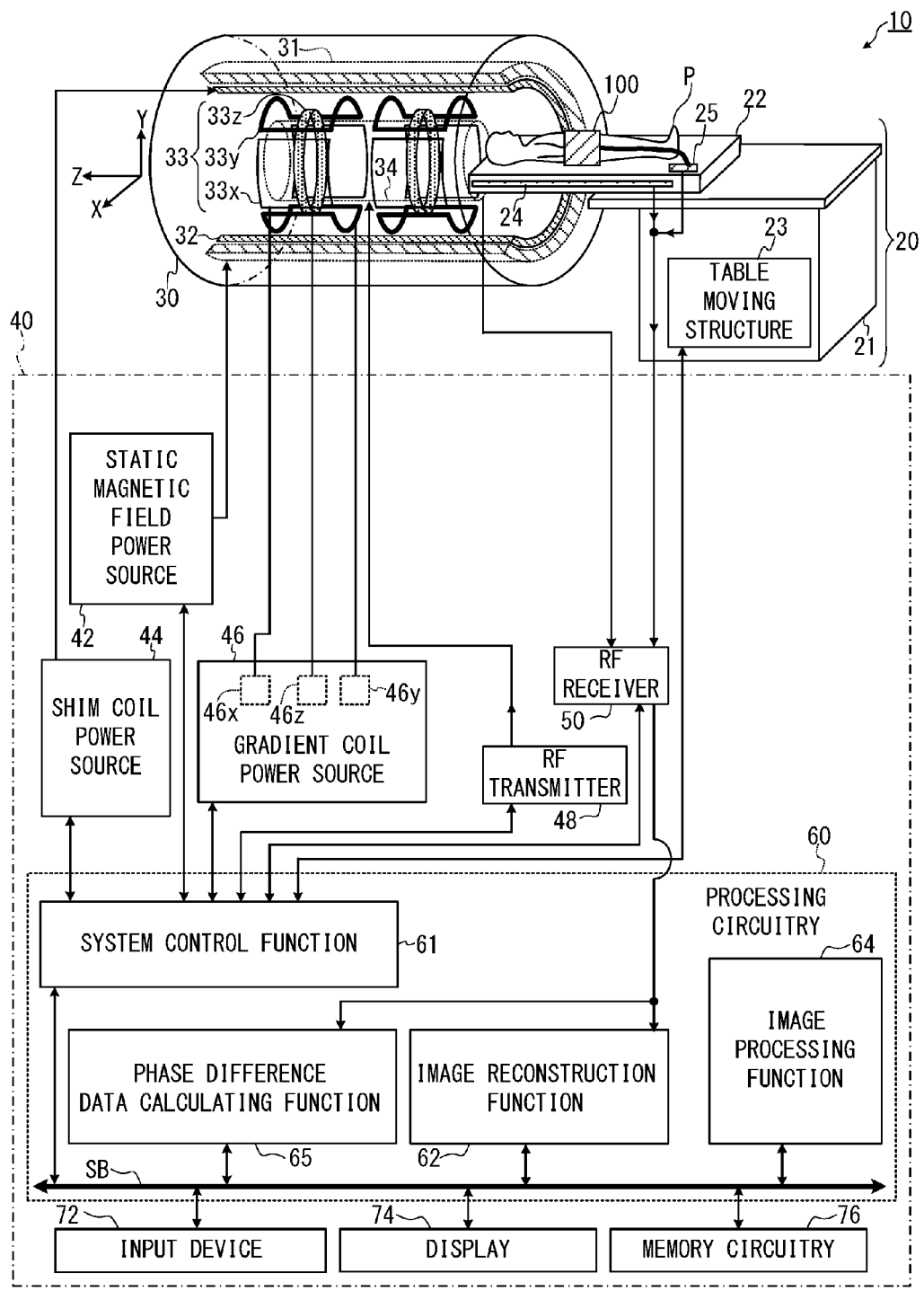
FIG. 1 is a block diagram showing an example of overall configuration of the MRI apparatus of the present embodiment.

FIG. 1 is a block diagram showing an example of overall configuration of the MRI apparatus 10 according to the present embodiment. As an example here, the components of the MRI apparatus 10 will be explained by sorting them into three groups: a bed 20, a gantry 30, and a control device 40.

Firstly, the bed 20 includes a supporting platform 21, a table 22, and a table moving structure 23 disposed inside the supporting platform 21. An object P is loaded on the top surface of the table 22. In addition, a reception RF coil 24 receiving MR signals from the object P is disposed inside the table 22. Moreover, plural connection ports 25 each of which can be connected to a wearable type RF coil 100 are disposed on the top surface of the table 22.

The supporting platform 21 supports the table 22 in such a manner that the table 22 can move in the horizontal direction (i.e. along the Z axis direction of the apparatus coordinate system).

The table moving structure 23 adjusts the position of the table 22 in the vertical direction by adjusting the height of the supporting platform 21, when the table 22 is outside the gantry 30.

In addition, the table moving structure 23 inserts the table 22 into inside of the gantry 30 by moving the table 22 in the horizontal direction and moves the table 22 to outside of the gantry 30 after completion of imaging.

Secondly, the gantry 30 is shaped in the form of a cylinder, for example, and is installed in an imaging room. The gantry 30 includes a static magnetic field magnet 31, a shim coil 32, a gradient coil 33, and an RF coil 34.

The static magnetic field magnet 31 is, for example, a superconductivity coil and shaped in the form of a cylinder. The static magnetic field magnet 31 forms a static magnetic field in an imaging space by consuming electric currents supplied from the static magnetic field power source 42 as described below.

The above-described imaging space means, for example, a space in the gantry 30 in which the object P is placed and to which the static magnetic field is applied. The static magnetic field power source 42 may be omitted by configuring the static magnetic field magnet 31 as a permanent magnet.

The shim coil 32 is, for example, shaped in the form of a cylinder and arranged inside the static magnetic field magnet 31 so as to become coaxial with the static magnetic field magnet 31. The shim coil 32 forms an offset magnetic field, which uniforms the static magnetic field, by using electric currents supplied from the shim coil power source 44 of the control device 40 described below.

The gradient coil 33 is, for example, shaped in the form of a cylinder and arranged inside the shim coil 32. The gradient coil 33 includes an X axis gradient coil 33$x$, a Y axis gradient coil 33$y$, and a Z axis gradient coil 33$z$.

In this specification, the X axis, the Y axis, and the Z axis are assumed to be those of the apparatus coordinate system unless otherwise specifically noted. As an example here, the apparatus coordinate system, whose X axis, Y axis and Z axis are perpendicular to each other, is defined as follows.

First, the Y axis direction is defined as the vertical direction, and the table 22 is disposed in such a position that the direction of the normal line of its top surface becomes identical to the Y axis direction. The horizontal moving direction of the table 22 is defined as the Z axis direction, and the gantry 30 is installed in such a manner that its axis direction becomes identical to the Z axis direction. The X axis direction is the direction perpendicular to these Y axis direction and Z axis direction, and is the width direction of the table 22 in the example of FIG. 1.

The X axis gradient coil 33$x$ forms a gradient magnetic field Gx in the X axis direction in an imaging region in accordance with an electric current supplied from the X axis gradient coil power source 46x described below. Similarly, the Y axis gradient coil 33y forms a gradient magnetic field Gy in the Y axis direction in the imaging region in accordance with an electric current supplied from the Y axis gradient coil power source 46y described below. Similarly, the Z axis gradient coil 33z forms a gradient magnetic field Gz in the Z axis direction in the imaging region in accordance with an electric current supplied from the Z axis gradient coil power source 46z described below.

Thereby, directions of a gradient magnetic field Gss in a slice selection direction, a gradient magnetic field Gpe in a phase encode direction, and a gradient magnetic field Gro in a readout (frequency encode) direction can be arbitrarily selected as logical axes, by combining the gradient magnetic fields Gx, Gy, and Gz in the X axis, the Y axis, and the Z axis directions as three physical axes of the apparatus coordinate system.

The above-described term "imaging region" means, for example, at least a part of an acquisition range of MR signals used to generate one image or one set of images, which becomes one or plural images. The imaging region is defined as a part of the imaging space in terms of range and position by an apparatus coordinate system, for example.

For example, when MR signals are acquired in a range wider than a region made into an image in order to prevent aliasing (artifact), the imaging region is a part of the acquisition range of MR signals. By contrast, in some cases, the entire acquisition range of MR signals becomes an image, i.e. the imaging region and the acquisition range of MR signals matches each other. In addition, the above one set of images means, for example, plural images when MR signals of plural images are acquired in a lump in one pulse sequence such as multi-slice imaging.

The RF coil 34 is, for example, shaped in the form of a cylinder and arranged inside the gradient coil 33. As an example here, the RF coil 34 is a whole body coil which combines a function of transmitting RF pulses and a function of receiving MR signals. However, the RF coil 34 may be composed of a transmission RF coil which exclusively performs transmission of RF pulses. Additionally, the RF coil 34 may be composed of the whole body coil and the transmission RF coil, for example.

Thirdly, the control device 40 includes the static magnetic field power source 42, the shim coil power source 44, a gradient coil power source 46, an RF (Radio Frequency) transmitter 48, an RF receiver 50, processing circuitry 60, an input device 72, a display 74, and memory circuitry 76.

The gradient coil power source 46 includes the X axis gradient coil power source 46x, the Y axis gradient coil power source 46y, and the Z axis gradient coil power source 46z.

The X axis gradient coil power source 46x supplies the X axis gradient coil 33x with an electric current for forming the gradient magnetic field Gx. The Y axis gradient coil power source 46y supplies the Y axis gradient coil 33y with an electric current for forming the gradient magnetic field Gy. The Z axis gradient coil power source 46z supplies the Z axis gradient coil 33z with an electric current for forming the gradient magnetic field Gz.

The RF transmitter 48 generates RF pulse electric currents of the Larmor frequency for causing nuclear magnetic resonance in accordance with control information inputted from the processing circuitry 60, and outputs the generated RF pulse electric currents to the RF coil 34. The RF pulses in accordance with these RF pulse electric currents are transmitted from the RF coil 34 to the object P.

The whole body coil (RF coil 34), the reception RF coil 24, and the wearable type RF coil 100 receive MR signals generated due to excited nuclear spin inside the object P by the RF pulses and the received MR signals are outputted to the RF receiver 50.

The RF receiver 50 generates raw data which are digitized complex number data of MR signals obtained by performing predetermined signal processing on the received MR signals and then performing A/D (analogue to digital) conversion on them.

The RF receiver 50 outputs the generated raw data of MR signals to an image reconstruction function 62 and a phase difference data calculating function 65 of the processing circuitry 60 described below.

The processing circuitry 60 includes structure for computational processing such as a processor. The processing circuitry 60 includes a system control function 61, a system bus SB, an image reconstruction function 62, an image processing function 64, and a phase difference data calculating function 65. The processing circuitry 60 implements each of the above-described functions, by executing programs stored in the memory circuitry 76 and/or programs directly stored in the processor of the processing circuitry 60.

The system control function 61 of the processing circuitry 60 performs system control of the MRI apparatus 10 in setting of imaging conditions of a main scan, an imaging operation, and image display after imaging through interconnection such as the system bus SB.

Specifically, the system control function 61 stores control information needed in order to cause the gradient coil power source 46, the RF transmitter 48, and the RF receiver 50 to drive. The above-described control information includes, for example, sequence information describing operation control information such as intensity, application period, and application timing of the pulse electric currents which should be applied to the gradient coil power source 46.

The system control function 61 drives the gradient coil power source 46, the RF transmitter 48, and the RF receiver 50 in accordance with a predetermined sequence stored, so that the gradient magnetic fields Gx, Gy and Gz are formed and RF pulses are transmitted.

The above-described imaging condition refers to under what condition RF pulses or the like are transmitted in what type of pulse sequence, or under what condition MR signals are acquired from the object P, for example. As parameters of the imaging conditions, for example, there are an imaging region as positional information in the imaging space, a flip angle, a repetition time TR, number of slices, an imaging part, and type of pulse sequence such as spin echo and parallel imaging. The above-described imaging part means a region of the object P to be imaged, such as the head, the chest, and the abdomen.

The above-described main scan is a scan for imaging an intended diagnosis image such as a T1 weighted image, and it does not include a scan for acquiring MR signals for a scout image or a tuning san (calibration scan). A scan is an operation of acquiring MR signals, and it does not include the image reconstruction processing.

The tuning scan is a scan for determining unconfirmed elements of imaging conditions of the main scan, conditions and data used for the image reconstruction processing and correction processing after the image reconstruction, and the tuning is performed separately from the main scan.

As an example of the tuning scan, a template scan in which phase correction data of EPI are obtained is known.

In addition, the system control function 61 of the processing circuitry 60 causes the display 74 to display screen information for setting imaging conditions, sets the imaging conditions based on command information from the input device 72. Furthermore, the system control function 61 causes the display 74 to display images indicated by the generated display image data after completion of imaging.

The input device 72 includes input tools such as a mouse and a keyboard, and further includes an input circuit which transmits contents inputted via the input tools to each component such as the processing circuitry 60. The input device 72 provides a user with a function to set the imaging conditions and image processing conditions.

The image reconstruction function 62 of the processing circuitry 60 arranges and stores the raw data of MR signals inputted from the RF receiver 50 as k-space data, in accordance with the phase encode step number and the frequency encode step number. The above-described k-space means a frequency space.

In the present embodiment, the image reconstruction function 62 generates k-space data which have been subjected to the regridding processing. Details of the regridding processing will be described below.

The image reconstruction function 62 reconstructs image data of the object P by performing the image reconstruction processing including Fourier transformation and the phase error correction as described below. The image reconstruction function 62 stores the reconstructed image data in the memory circuitry 76.

Incidentally, image data of MRI are composed so that each pixel has a pixel value, for example. The pixel value indicates, for example, the luminance level thereof when this pixel is displayed (indicates intensity of the MR signal received from the object region corresponding to this pixel). In the case of a slice, the number of pixels in height and width of image data of MRI becomes the phase encode number times the frequency encode number, for example.

The image processing function 64 of the processing circuitry 60 takes in the reconstructed image data from the memory circuitry 76, performs predetermined image processing on them, and stores the image data subjected to the image processing in the memory circuitry 76 as display image data.

The memory circuitry 76 stores the display image data after adding accompanying information such as the imaging conditions used for generating the display image data and information of the object P (patient information) to the display image data.

Incidentally, the four components including the processing circuitry 60, the input device 72, the display 74, and the memory circuitry 76 may be configured as one computer and disposed in an imaging room, for example.

In addition, though the components of the MRI apparatus 10 are sorted into three groups (the gantry 30, the bed 20 and the control device 40) in the above explanation, this is only an example of interpretation.

For example, the table moving structure 23 may be interpreted as a part of the control device 40.

Additionally, the RF receiver 50 may be included not outside the gantry 30 but inside the gantry 30. In this case, for example, an electronic circuit board which is equivalent to the RF receiver 50 may be disposed in the gantry 30. Then, the MR signals, which are analog electrical signals converted from the electromagnetic waves by the wearable type RF coil 100, the reception RF coil 24 and so on, may be amplified by a pre-amplifier in the electronic circuit board, then the amplified signals may be outputted to the outside of the gantry 30 as digital signals and inputted to the processing circuitry 60. In outputting the signals to the outside of the gantry 30, for example, an optical communication cable is preferably used to transmit the signals in the form of optical digital signals. This is because the effect of external noise is reduced.

Principle Explanation of the Present Embodiment

As an example in the present embodiment, three template scans A, B and C are performed for each slice or each slab as tuning scans. The template scan A is used only for acquisition of phase correction data. The template scan C is used only for the regridding processing. The template scan B is used for both of the regridding processing and the acquisition of the phase correction data.

Figure 2:
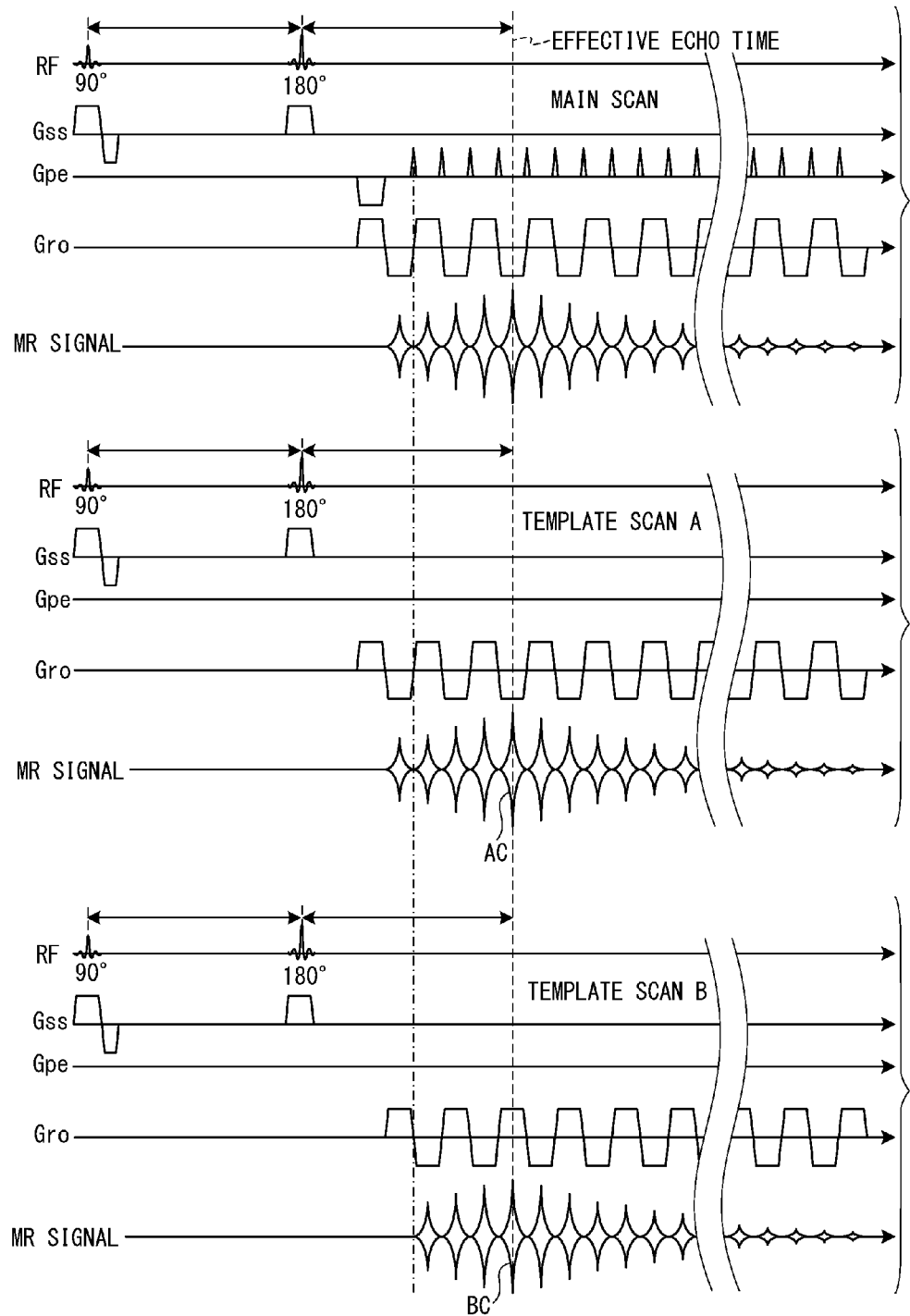
FIG. 2 is a timing diagram showing examples of respective pulse sequences for a main scan and template scans A and B for correcting phase errors.

FIG. 2 is a timing diagram showing examples of the respective pulse sequences for the main scan and the template scans A and B for correcting phase errors.

The upper part of FIG. 2 shows the pulse sequence for the main scan, the middle part of FIG. 2 shows the pulse sequence for the template scan A, the lower part of FIG. 2 shows the pulse sequence for the template scan B, and each horizontal axis indicates elapsed time t.

In each of the upper, middle, and lower parts of FIG. 2, RF represents an RF pulse, Gss represents the gradient magnetic field in the slice selection direction, Gpe represents the gradient magnetic field in the phase encode direction, Gro represents the gradient magnetic field in the readout direction, and MR SIGNAL represents an echo.

In the main scan shown in the upper part of FIG. 2, single-shot EPI of spin-echo type is used as an example. In this example, an excitation (RF) pulse with a flip angle of 90° is applied, and then a refocusing pulse with a flip angle of 180° is applied. Afterward, MR signals are acquired by repeating inversion of the polarity of the gradient magnetic field pulses Gro in the readout direction. During that period, after application of one prepulse as the gradient magnetic field Gpe in the phase encode direction, a blip pulse whose polarity is opposite to the prepulse is applied as the gradient magnetic field Gpe in the phase encode direction each time polarity of the gradient magnetic field pulses Gro in the readout direction is inversed. Thereby, phase encode amount is added in order.

The area (the time integral value of absolute values of intensity) of the prepulse of the gradient magnetic field Gpe in the phase encode direction is equal to the total area of the first four blip pulses. In other words, at the application timing of the fourth blip pulse, the phase encode amount becomes zero. In this example, because the phase encode step of the MR signal fifthly acquired in the main scan is zero and this fifthly acquired MR signal corresponds to the effective echo time determined by application timing of the excitation pulse and the refocusing pulse, the intensity of this fifthly acquired MR signal becomes the maximum.

As an example here, the pulse sequence of the template scan A is the same as the pulse sequence of the main scan except the following two points.

As the first different point, in the template scan A, the gradient magnetic field Gpe in the phase encode direction is not applied for the following reason. Consider a case where plural lines near the center line of a k-space are used for correcting phase errors. In this case, if the gradient magnetic field Gpe in the phase encode direction is applied, the phase shift in the readout direction cannot be accurately calculated. This is because the phase shift (phase deviation) of the gradient magnetic field Gpe in the phase encode direction is also included in each of the MR signals and this phase shift is different for each MR signal arranged to each position of the phase encode axis in the k-space.

However, as an example in the present embodiment, since only the data of the center line of the k-space are used for correcting phase errors, the difference in phase shift of the gradient magnetic field Gpe in the phase encode direction between the respective lines of the MR signals causes little influence. Thus, when only the MR signal of one line of a k-space is used for correcting phase errors, though the gradient magnetic field Gpe in the phase encode direction may be applied, it is preferable to avoid applying the gradient magnetic field Gpe in the phase encode direction like the present embodiment.

As the second different point, an acquisition region of the MR signals (FOV: Field Of View) in the template scan A is expanded only in the readout direction from the main scan, so as to include, for example, the center of the FOV of the main scan. As to the degree of expansion, it will be described below. Here, it is not possible to reconstruct an image from the k-space data obtained by the template scan A in which the gradient magnetic field Gpe in the phase encode direction is not applied. Thus, in a precise sense, it is not accurate to describe an acquisition region of the MR signals of the template scan A as FOV.

Since the differences are only the above two points, an acquisition region of MR signals of the template scan A in the phase encode direction and the slice selection direction is the same as that of the main scan (since the gradient magnetic field Gpe in the phase encode direction is not applied in the template scan A, the phase encode direction of the template scan A is a direction orthogonal to both the readout direction and the slice selection direction, in a precise sense).

In addition, in the template scan A, the fifthly acquired MR signal AC as an odd number-th echo (the middle part of FIG. 2) has the maximum intensity and is arranged at the center line in the k-space data. This point is the same as the main scan, including the effective echo time based on each application timing of an excitation pulse and an refocusing pulse.

The template scan B is the same pulse sequence as the template scan A, except the following two points.

As the first difference, in the template scan B, the fourthly acquired MR signal BC (the lower part of FIG. 2) as an even number-th echo has the maximum intensity and is arranged at the center line in the k-space data.

In other words, the start timing of applying the gradient magnetic field Gro in the readout direction in the template scan B is delayed from that of the template scan A by a Gro inversion interval.

Thereby, the start timing of generating the MR signal based on the application timing of the 90° excitation pulse in the template scan B is delayed from the template scan A by the Gro inversion interval.

The above-described "Gro inversion interval" means a length of time required after the polarity of the gradient magnetic field Gro in the readout direction is inverted and before the polarity is inverted again. In addition, the above-described "start timing of applying" means, for example, the timing whose reference is start time of applying an excitation pulse. As an example here, the start timing of applying the excitation pulse and the start timing of applying the refocusing pulse are common to the main scan and the template scans A, B, and C.

As the second difference, in the template scan B, the polarity of the gradient magnetic field Gro in the readout direction at the start of application is determined so that the polarity of the gradient magnetic field Gro in the readout direction at the timing of the effective echo time becomes inverse to that of the template scan A. This is because the phase error component due to non-uniformity of the static magnetic field is easily eliminated in the case of satisfying the above condition and it is preferable in terms of obtaining the phase correction data.

More specifically, the main causes of the phase errors in EPI are considered to be the following two: non-uniformity of a static magnetic field and eddy magnetic field generated by switching of magnetic fields. The phase error component caused by the non-uniformity of the static magnetic field is canceled by subtraction between data of the template scan A and data of the template scan B, because the respective polarities of the gradient magnetic field Gro in the readout direction at the timing of the effective echo time in the template scans A and B are inverse to each other. Thereby, phase error components caused by other reasons can be extracted.

In order to satisfy the above condition, the polarity of the gradient magnetic field Gro in the readout direction at the timing of the effective echo time indicated by the vertical broken line in FIG. 2 is minus in the template scan A (as shown by the generation timing of the fifth MR signal AC in the middle part of FIG. 2), and is plus in the template scan B (as shown by the generation timing of the fourth MR signal BC in the lower part of FIG. 2).

Next, the degree of expanding an acquisition region of the MR signals in the template scans A and B will be explained. For example, when the length of FOV in the phase encode direction and the length of FOV in the readout direction are equal to each other in the main scan, the acquisition region of the MR signals in each of the template scans A and B is expanded in the readout direction twice as large as the main scan.

As to expansion of FOV in the readout direction, it is preferable to be degree of not causing wraparound by shifting the acquisition region of the MR signals of the template scan C (to be described below) in the readout direction. Thus, as a rough guide of degree of expansion, for example, twice the main scan is desirable.

Incidentally, if the object region is substantially the center of the FOV and the rate of the region occupied by the object is small compared with the entire FOV, the rate of expanding FOV in the readout direction may be smaller than double.

In addition, as to expansion of FOV in the readout direction, it is preferable that the same image resolution as the main scan is maintained after expanding FOV in the readout direction. The reason is as follows.

The result of the template scan B is used for the regridding processing together with the template scan C, as mentioned above. The aim of the template scans B and C is to accurately calculate distortion of the waveform of the gradient magnetic field Gro in the readout direction in the main scan.

Thus, it is easier to accurately calculate the waveform of the gradient magnetic field Gro in the readout direction in the main scan from the execution results of the template scans B and C if each condition of the template scans B and C such as the time interval of inversion of the gradient magnetic field Gro in the readout direction and wave height (the maximum intensity) is the same as each condition in the main scan.

In addition, since the template scan B is used for correcting phase errors together with the template scan A, it is desired that each of the acquisition regions of the MR signals of the template scans A and B should be equal to each other.

For the above reasons, it is preferable to set the frequency encode step number of the template scans A and B twice as many as the main scan when the acquisition regions of the MR signals of the template scans A and B are expanded in the readout direction from the main scan.

As an example in the present embodiment, it is assumed that the phase encode step number and the frequency encode step number are both 256 in the main scan and the frequency encode step number in the template scans A and B is 512. Thus, in each of the template scans A and B, the amount of the MR signals acquired by inverting the gradient magnetic field Gro in the readout direction is twice as many as the main scan.

Next, prior to explanation of how to calculate the phase correction data for correcting the phase errors, an example of a method of generating the k-space data regarding the concept of calculating the phase correction data will be explained.

Figure 3:
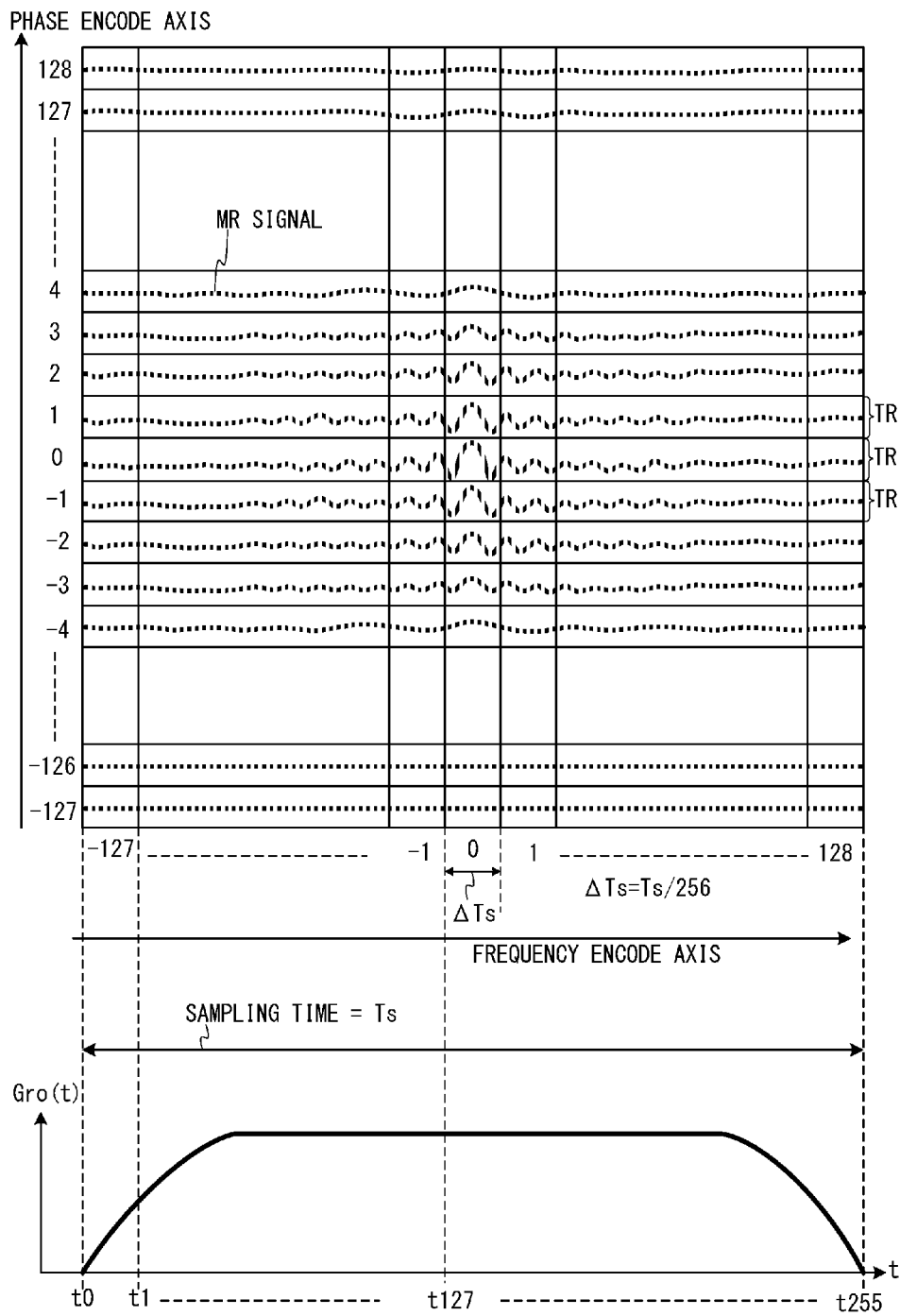
FIG. 3 is a schematic diagram showing an example of a method of generating k-space data, when the number of phase encode and frequency encode matrix elements is 256 by 256.

FIG. 3 is a schematic diagram showing an example of a method of generating the k-space data when the number of phase encode and frequency encode matrix elements is 256 by 256. The upper part of FIG. 3 shows a real part or an imaginary part of the k-space data, and the lower part of FIG. 3 shows an example of a gradient magnetic field pulse in the readout direction.

In the upper part of FIG. 3, TR represents a repetition time, and the vertical axis indicates the phase encode axis in a k-space. Each number at the right side of the vertical axis is the phase encode step number when the gradient magnetic field Gpe in the phase encode direction is applied like the main scan. The horizontal axis in the upper part of FIG. 3 is the frequency encode axis in a k-space.

In addition, Ts in the horizontal direction in FIG. 3 indicates sampling time. In the lower part of FIG. 3, the horizontal axis indicates elapsed time t (i.e. sampling time t), and the vertical axis indicates magnetic field intensity of the gradient magnetic field pulse in the readout direction.

In a pulse sequence according to the ordinary spin echo technique, the gradient magnetic field Gpe in the phase encode direction is changed, for example, 256 times to acquire 256 lines of MR signals, and a cosine function of the carrier frequency is subtracted from each of the MR signals. The 256 MR signals processed in this way are arranged in the order of the phase encode step from the bottom, such as −127, −126, . . . , −1, 0, 1, . . . , 127, 128 as shown in the upper part of FIG. 3.

Furthermore, a line of each MR signal is divided into 256 parts at equal interval of ΔTs in the direction of the frequency encode axis (the direction of the sampling time t) of the upper part of FIG. 3, and intensity of each of the 256 parts of the divided MR signal is converted into a matrix value. In this way, matrix data formed by 256 by 256 matrix elements, i.e. the real part of the k-space data are obtained.

In addition, the imaginary part of the k-space data consisting of 256 by 256 matrix elements can be obtained in the same way as above except that a sine function of the carrier frequency is subtracted instead of the cosine function of the carrier frequency.

By contrast, in the single shot EPI like the upper part of FIG. 2, if only four lines of MR signals are acquired before the timing of the zero phase encode step, the number of lines of MR signals to be acquired is 132 (256/2+4). As an example in this case, zero as data in the k-space is assigned to each of the 124 lines of the MR signals that are not acquired.

Incidentally, since the gradient magnetic field Gpe in the phase encode direction is not applied in the template scans A and B, the phase encode amount is common to all the 256 lines of the MR signals filled in the k-space.

Next, the calculation method of the phase correction data for correcting the phase errors will be explained. In the following explanation, the k-space data obtained from the MR signals acquired in the template scan A are referred to as the template data A. Similarly, the k-space data obtained from the MR signals acquired in the template scan B are referred to as the template data B, and the k-space data obtained from the MR signals acquired in the template scan C are referred to as the template data C.

Firstly, consider the real part of the template data A (i.e. the k-space data obtained by subtracting the cosine wave of the carrier frequency from each the MR signal of the template scan A). As an example here, only the center line of the k-space data is used. In the template scan A, the frequency encode step number is 512.

Thus, the center line of the real part of the template data A (corresponding to the MR signal AC at the effective echo time in FIG. 2) is divided into 512 parts in the frequency encode axis direction, and thereby intensity of the MR signal is sampled.

This processing may be interpreted as dividing time interval from start time t0 of applying the gradient magnetic field Gro in the readout direction to application ending time t511 into 512 parts (note that t0 is an inversion time and t511 is re-inverting time in the case of EPI). Note that in the lower part of FIG. 3 that indicates the same concept as above, the MR signal is divided into 256 parts of sampling time t0 to sampling time t255, because the frequency encode step number of the main scan is 256.

In this manner, the MR signal at the effective echo time is divided into 512 parts corresponding to the respective sampling times t0 to t511, and data of intensity of each of these divided parts are defined as the real number data KAreal(kr) of the center line of the template data A. Here, kr is a spatial frequency [radian/meter] in the readout direction, and (kr) means a function of a spatial frequency kr (the same holds true for the other parameters in the explanation below).

Thus, though KAreal(kr) is a function of a spatial frequency kr in the readout direction in a precise sense, it may be interpreted as a function of sampling time t. Around t255 whose sampling time is close to the center of the k-space, intensity of the MR signal is strong, information amount is large, and the spatial frequency kr in the readout direction becomes data of a low-frequency region. On the other hand, around t0 or t511 whose sampling time is the edge side of the k-space, intensity of the MR signal is weak and the acquired data are in a high-frequency region.

The imaginary number data KAimag(kr) of the center line of the template data A can be obtained by dividing the MR signal of the center line of the imaginary part of the template data A into 512 parts in the frequency encode axis direction and performing the sampling processing in a similar manner as described above. Thus, by defining an imaginary unit as j, complex data KA(kr) of the center line of the template data A can be obtained by the next formula.

$$KA(kr)=KAreal(kr)+\{j \times KAimag(kr)\} \quad (1)$$

After calculating the real number data KBreal(kr) of the center line of the template data B and the imaginary number data KBimag(kr) of the center line of the template data B in a similar manner as described above, the complex data KB(kr) of the center line of the template data B can be obtained by the next formula.

$$KB(kr)=KBreal(kr)+\{j \times KBimag(kr)\} \quad (2)$$

Next, by performing one-dimensional inverse Fourier transformation on the complex data KA(kr) of the center line of the template data A in the frequency encode axis direction of the k-space, their real-space data RA(xr) can be obtained.

Similarly, by performing one-dimensional inverse Fourier transformation on the complex data KB(kr) of the center line of the template data B in the frequency encode axis direction of the k-space, their real-space data RB(xr) can be obtained.

The (xr) in the real-space data RA(xr) and RB(xr) means a function of a position xr [meter] in the readout direction (the same holds true for the other parameters in the explanation below). Both of the real-space data RA(xr) and the real-space data RB(xr) are complex data.

Here, the effective echo time is common to the template data A and B as the generation sources of the real-space data RA(xr) and RB(xr), and the polarity of the gradient magnetic field Gro in the readout direction at detection of the MR signals is opposite to each other between the template data A and B. Thus, the phase error component caused by non-uniformity of the static magnetic field included in the phase component of the real-space data RA(xr) is equal to that of the real-space data RB(xr).

Next, the complex conjugate number of QQ is defined as {QQ}*. Then, the phase correction data dV(xr) for correcting the phase errors is given by the following formula (3).

$$dV(xr) = \frac{RA(xr) \times \{RB(xr)\}^*}{|RA(xr) \times \{RB(xr)\}^*|} \quad (3)$$

The above formula (3) gives a unit vector, which has a phase equal to the phase difference between two vectors RA(xr) and RB(xr), and whose absolute value is one. Thus, the phase error component caused by the non-uniformity of the static magnetic field is eliminated by the phase correction data dV(xr) given by the formula (3), and only the rest of phase error components can be extracted.

Next, the k-space data of the main scan obtained by, for example, the method shown in FIG. 3 is defined as KM(shot, echo, kr). Here, "shot" means the shot number at which the k-space data are acquired (i.e. the number indicating the order of the scan), and "echo" means the order at which the data of the MR signal are acquired after application of an excitation pulse. For example, in the case of the MR signal acquired at the effective echo time in the upper part of FIG. 2, echo=5.

Next, the real-space data obtained by performing one-dimensional inverse Fourier transformation on the k-space data KM(shot, echo, kr) of the main scan in the frequency encode axis direction of the k-space is defined as RM(shot, echo, xr).

The real-space data obtained by performing the phase error correction on the real-space data RM(shot, echo, xr) of the main scan is defined as RM'(shot, echo, xr).

As an example here, in the real-space data RM(shot, echo, xr) of the main scan, the phase error correction is not performed on data whose echo number is odd but performed only on data whose echo number is even. In the case of an even-numbered echo, its phase error is corrected by the next formula in which complex conjugate number data of the phase correction data dV(xr) are used.

$$RM'(\text{shot,echo,}xr)=RM(\text{shot,echo,}xr) \times \{dV(xr)\} \quad (4)$$

In other words, in the real-space data RM(shot, echo, xr) of the main scan, discontinuity between phases of respective MR signals is reduced by returning the obtained error component only to the even-numbered MR signals (echoes) with the use of the formula (4). The phase errors due to factors except the non-uniformity of the static magnetic field have a first-order gradient in the readout direction of the real-space mainly, and the direction of a phase gradient is reversed by the polarity of the gradient magnetic field Gro in the readout direction in an acquisition period of MR signals. The above correction method is on the assumption of this regularity.

Although the method of calculating the phase correction data dV(xr) is novel, correction of the phase errors after calculating the phase correction data dV(xr) may be the same as conventional technology, and further explanation is omitted. Thus, the above method of correcting the phase errors is only an example and another method may be used.

Figure 4:
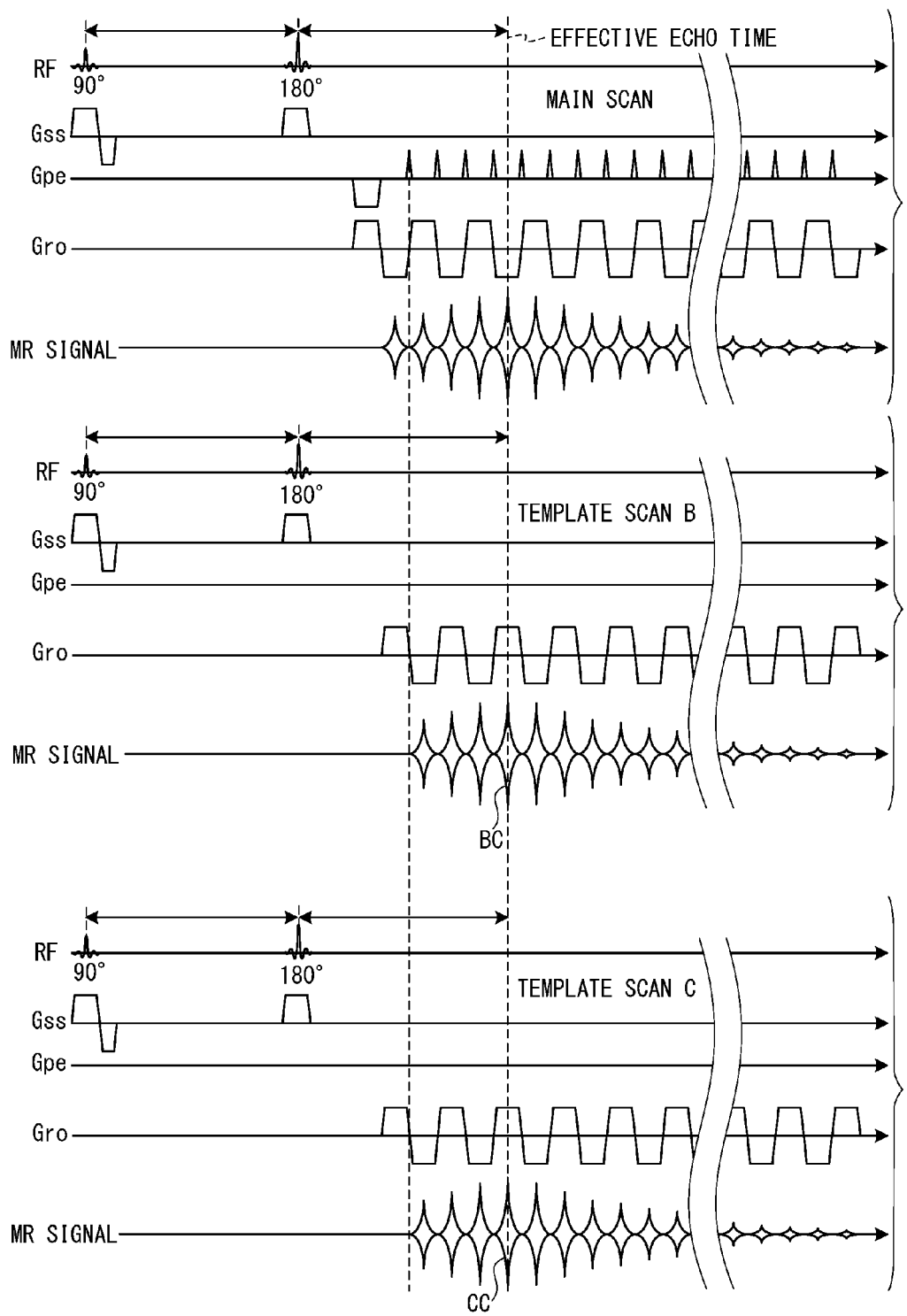
FIG. 4 is a timing diagram showing examples of the respective pulse sequences for the main scan and the template scans B and C for the regridding processing.

FIG. 4 is a timing diagram showing examples of the respective pulse sequences for the main scan and the template scans B and C for the regridding processing. The upper part of FIG. 4 indicates the pulse sequence of the main scan, the middle part of FIG. 4 indicates the pulse sequence of the template scan B, and the bottom part of FIG. 4 indicates the pulse sequence of the template scan C. The notation in FIG. 4 is the same as FIG. 2, and the pulse sequences of the main scan and the template scan B in FIG. 4 are the same as FIG. 2.

The template scan C is the same as the template scan B except the following one point. The acquisition region of the MR signals of the template data C is shifted by a predetermined interval in the readout direction, from the acquisition region of the MR signals of the template data B.

It is desirable that the shift amount of the acquisition region of the MR signals in the readout direction is, for example, approximately five pixels to 10 pixels, for the following two reasons.

Firstly, if the shift amount is only one pixel, there is a possibility that the phase difference data Δθ(t) between the template data B and the template data C cannot be satisfactorily precisely calculated because the phase difference between them does not sufficiently appear.

Secondly, if the shift amount in the readout direction is too large like, for example, an approximate half of an image, back-folding of phase data frequently occurs and the phase difference data Δ (t) between the template data B and the template data C cannot be satisfactorily precisely calculated.

In order to shift the acquisition region of the MR signals in the readout direction, it can be achieved by shifting the frequency of the carrier wave used at the time of phase detection of the MR signals by the frequency in proportion to the shift amount towards the readout direction. For example, when magnitude of the gradient magnetic field pulse in the readout direction in an acquisition period of MR signals is defined as IGro [Tesla/meter], the shift amount of the acquisition region of MR signals in the readout direction is defined as r0 [meter], and the gyromagnetic ratio of a hydrogen atom is defined as γ [radian/(Tesla*second)], the frequency shift amount Δf [Hz] of the carrier wave is indicated by the following formula.

$$\Delta f = \gamma / \{2\pi \times IGro \times r0\} \quad (5)$$

In other words, when the detection frequency of the RF receiver 50 during the acquisition period of the MR signals under the template scan B (i.e. the frequency of the carrier wave) is, for example, the Larmor frequency of the magnetic field center, the detection frequency for the template scan C is obtained by shifting the Larmor frequency of the magnetic field by Δf.

In the present embodiment, the phase difference data A (t) in the readout direction for the regridding processing is calculated as a function of elapsed time t from start time of applying the gradient magnetic field pulse in the readout direction, and the waveform of the gradient magnetic field pulse in the readout direction is precisely calculated based on the phase difference data Δθ(t). In the present embodiment, accuracy of the regridding processing is improved by performing the regridding processing based on the waveform of the gradient magnetic field pulse in the readout direction precisely calculated in this way.

Note that (t) means a function of sampling time t (the same hold true for other parameters in the explanation below). In addition, the phase difference data Δθ(t) for the regridding processing is a function of the spatial frequency kr in the readout direction in a precise sense, because these data use k-space data.

However, the phase difference data Δθ(t) can also be regarded as a function of sampling time t based on the formula (10) described below, because the MR signals are acquired under the condition where the spatial frequency is changed during their acquisition period. Here, the phase difference data Δθ(t) are treated as the function of sampling time t in terms of a magnetic field waveform.

Hereinafter, it will be explained in the order of the calculation method of the phase difference data Δθ(t) in the readout direction, the calculation method of the waveform of the gradient magnetic field pulse in the readout direction, and the method of the regridding processing.

First, a value of a matrix element of the real part of the k-space data at the time t of the line of the phase encode step PS is defined as KR(PS, t).

Similarly, a value of a matrix element of the imaginary part of the k-space data at the time t of the line of the phase encode step PS is defined as KI(PS, t).

The above time t is the sampling time t in the bottom part of FIG. 3. In each of the template scans B and C, the acquisition region of the MR signals is expanded in the readout direction to, for example, twice the main scan. Thus, in the template scans B and C, the frequency encode step number is increased to twice the main scan.

A total of 512 sampling times t0, t1, t2, . . . t511 in the order of earlier sampling time t correspond to the frequency encode steps −255 to 256, respectively. Time t0 is the start time of applying the gradient magnetic field pulse in the readout direction, time t511 is the ending time of applying the gradient magnetic field pulse in the readout direction. Incidentally, the frequency encode step number in the bottom part of FIG. 3 is indicated as not 512 but 256, because FIG. 3 corresponds to the main scan.

Thus, for example, the value of the matrix element, which corresponds to the earliest detection timing in the center line (i.e. the MR signal arranged at the center line) of the real part of the k-space data, is indicated by KR(0, t0). Note that the center line of the k-space data corresponds to the MR signal detected at the timing of the effective echo time and is also the line whose phase encode step is zero in the case of the main scan.

Similarly, the value of the matrix element, which corresponds to the final detection timing in the center line of the real part of the k-space data, is indicated by KR(0, t511).

Similarly, the value of the matrix element, which corresponds to the earliest detection timing in the center line of the imaginary part of the k-space data, is indicated by KI(0, t0).

In the k-space data, intensity of each MR signal at the time of detection is the strongest at the center line, and SN (Signal to Noise) ratio is the highest at the center line. Accordingly, as an example here, the phase data θ(t) in the readout direction are calculated by using the respective center lines of the real part and imaginary part of the k-space data.

For example, the respective phase data θ(t) at time t0 and time t1 are calculated under the following formulas (6) and (7) in which arc tangent is used.

$$\theta(t0)=\arctan\{KI(0,t0)/KR(0,t0)\} \quad (6)$$

$$\theta(t1)=\arctan\{KI(0,t1)/KR(0,t1)\} \quad (7)$$

A total of 512 phase data θ(t) from time t0 to time t511 can be calculated as functions of sampling time t in a similar manner as described above.

Then, the phase data θ(t) in the readout direction obtained from the center line of the template data B in the above manner are defined as θb(t), and the phase data θ(t) in the readout direction obtained from the center line of the template data C in the above manner are defined as θc(t).

Since both of the phase data θb(t) and θc(t) in the readout direction are data of the center lines and correspond to even number-th echo (the fourth echo in FIG. 4), the polarity of the gradient magnetic field Gro in the readout direction during the detection period of the corresponding MR signal is the same between both phase data θb(t) and θc(t). Thus, influence on phase due to non-uniformity of magnetic field can be canceled by simply using the difference between both. Accordingly, the phase difference data Δθ(t) in the readout direction can be calculated by using the following formula.

$$\Delta\theta(t)=\theta b(t)-\theta c(t) \quad (8)$$

Next, the spatial frequency kr(t) in the readout direction is indicated by the following formula.

$$kr(t)=\Delta\theta(t)/r0 \quad (9)$$

In addition, it is assumed that sampling time t begins at the start time of applying the gradient magnetic field pulse in the readout direction, and magnetic field intensity [Tesla/meter] of the gradient magnetic field pulse in the readout direction is defined as Gro(t) as a function of sampling time t. Then, the spatial frequency kr(t) in the readout direction at arbitrary sampling time t is given by the following formula.

$$kr(t)=\gamma\cdot\int Gro(t)dt \quad (10)$$

In the above formula (10), γ is the above-described gyromagnetic ratio of an hydrogen atom. The next formula is established by performing time-differentiation of the formula (10) with sampling time t.

$$Gro(t)=\{dkr(t)/dt\}/\gamma \quad (11)$$

The next formula is established by substituting the formula (9) into the formula (11).

$$Gro(t)=\{d\Delta\theta(t)/dt\}/(\gamma\times r0) \quad (12)$$

The waveform of the gradient magnetic field pulse in the readout direction Gro(t) can be precisely calculated under the formula (12), by calculating the phase difference data Δθ(t) from the template data B and the template data C.

Although data of the center line in the k-space data which have the maximum signal intensity are used in the above example, embodiments of the present invention are not limited to such an aspect.

For example, the phase difference data $\Delta\theta(t)$ in the readout direction may be calculated out plural times by using plural lines in the vicinity of the center line (plural lines in a low-frequency region where signal intensity is strong) and then the conclusive phase difference data $\Delta\theta(t)$ may be determined by averaging them. In the case of this modification of the present embodiment, accuracy of the phase difference data $\Delta\theta(t)$ can be further improved by taking an average.

In addition, an example in which the gradient magnetic field Gpe in the phase encode direction is not applied in the template scans B and C has been explained. However, embodiments of the present invention are not limited to such an aspect. As mentioned above, when the phase difference data $\Delta\theta(t)$ in the readout direction for the regridding processing are calculated only from the center line of the k-space data, the gradient magnetic field Gpe in the phase encode direction may be applied in the template scans B and C.

However, when plural lines in the k-space data are used for calculation of the phase difference data $\Delta\theta(t)$, it is preferable that the gradient magnetic field Gpe in the phase encode direction is not applied in the template scans B and C. If the gradient magnetic field Gpe in the phase encode direction is applied in the template scans B and C, it becomes difficult to precisely calculate the phase shift in the readout direction because the phase shift in the phase encode direction is included in the MR signals and degree of phase shift in the phase encode direction is different from one echo to another.

Next, as to methods of the regridding processing, two examples will be explained.

The value of each of the matrix elements of the k-space data obtained by sampling the MR signals at unequal or equal intervals under application of the gradient magnetic field Gro in the readout direction corresponds to the time-integrated quantity obtained by integrating the absolute value of intensity of the gradient magnetic field Gro in the readout direction in the time axis direction (i.e. corresponds to 0th-order moment of the gradient magnetic field Gro in the readout direction), on the k-space.

Although the 0th-order moment linearly changes in a region where a waveform of a gradient magnetic field is flat, the 0th-order moment in a region where a waveform of a gradient magnetic field is not flat is non-linear. Since image reconstruction presupposes that sampled data exist in a linear region of the k-space, it is desirable that non-linearly sampled data are corrected to become liner in the k-space.

Figure 5:
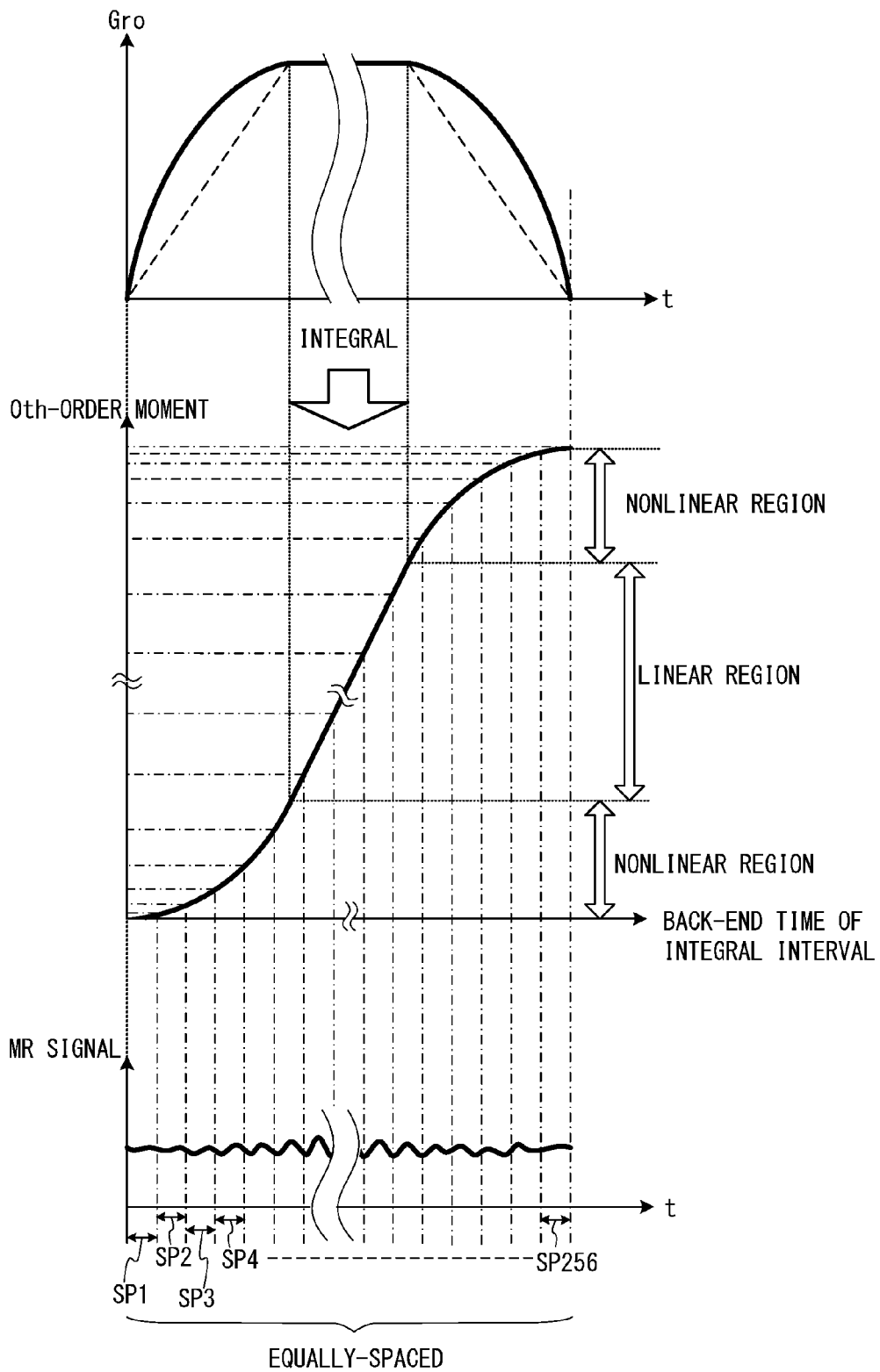
FIG. 5 is a conceptual diagram showing that MR signals sampled at equal time intervals in a region where intensity of the gradient magnetic field Gro in the readout direction is nonlinear are placed at unequal intervals in the k-space.

FIG. 5 is a conceptual diagram showing that MR signals sampled at equal time intervals in a region, where intensity of the gradient magnetic field Gro in the readout direction is nonlinear, are placed at unequal intervals in the k-space.

The upper part of FIG. 5 shows an example of the waveform of the gradient magnetic field Gro in the readout direction accurately calculated based on the phase difference data $\Delta\theta(t)$ in the readout direction for the above-described regridding processing. In other words, in the upper part of FIG. 5, the horizontal axis indicates elapsed time t from the start time of applying the pulses of the gradient magnetic field Gro in the readout direction (it is the same as the above sampling time t), and the vertical axis indicates the magnetic field intensity of the gradient magnetic field Gro in the readout direction.

The middle part of FIG. 5 shows a time integral of the absolute value of the magnetic field intensity of the gradient magnetic field Gro in the readout direction shown in the upper part of FIG. 5. In common to all the integration periods, the start time of the integration period is the start time of application of the pulses of the gradient magnetic field Gro in the readout direction.

Therefore, in the middle part of FIG. 5, the horizontal axis indicates the ending time of the integral interval (integration period), and the vertical axis indicates the time integral of the absolute value of the magnetic field intensity of the gradient magnetic field Gro in the readout direction, i.e. the 0th-order moment.

The lower part of FIG. 5 is a schematic diagram showing each sampling period for each of the MR signals for one phase encode step (i.e. the MR signals for one line), when sampling of the MR signals is performed based on equally-spaced sampling periods.

In the lower part of FIG. 5, the horizontal axis indicates elapsed time t from the start time of applying the pulses of the gradient magnetic field Gro in the readout direction like the upper part, and the vertical axis indicates the intensity of each MR signal. In this example, the number of frequency encode steps is 256, and 256 sampling periods SP1, SP2, SP3, SP4, . . . , SP256 are set. In other words, an MR signal for one line is equally divided into the 256 sampling periods SP1 to SP256 as shown by the vertical chain lines in FIG. 5.

The region where the gradient magnetic field is not flat means a region where the 0th-order moment of the gradient magnetic field is nonlinear, and the region where the gradient magnetic field is linear means a region where the 0th-order moment of the gradient magnetic field is linear.

Therefore, as can be seen from the upper part, the middle part, and the lower part of FIG. 5, if the MR signals are sampled at equal time intervals both in the region where the gradient magnetic field Gro in the readout direction is flat and in the region where the gradient magnetic field Gro in the readout direction is not flat, the generated k-space data become unequally-spaced in the k-space.

This is because the MR signals sampled under application of the gradient magnetic field Gro in the readout direction correspond to the 0th-order moment of the gradient magnetic field Gro in the readout direction in the k-space, and the 0th-order moment is unequally-spaced as shown by the horizontal chain lines in the middle part of FIG. 5.

Note that, in the following description, if the term "0th-order moment" is merely used, it means the 0th-order moment of the gradient magnetic field Gro in the readout direction.

Figure 6:
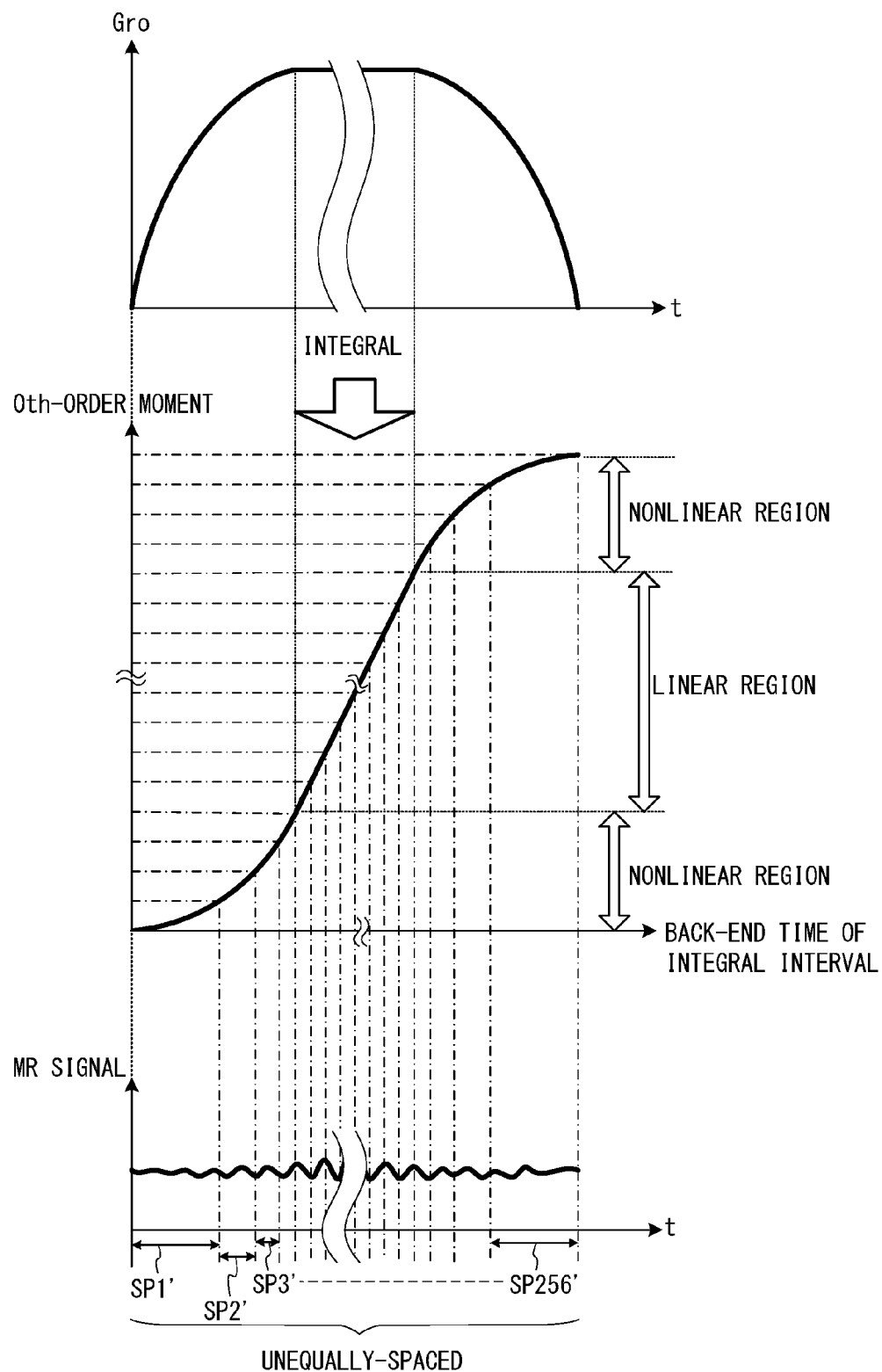
FIG. 6 is a schematic diagram showing concept of the first method of the regridding processing of the present embodiment.

FIG. 6 is a schematic diagram showing a concept of the first method of the regridding processing of the present embodiment. The upper part of FIG. 6 is the same as the upper part of FIG. 5. The lower part of FIG. 6 is a schematic diagram showing the sampling period for each of the MR signals for one phase encode step which are sampled at unequal intervals.

According to the first method, the MR signals for one line are unequally divided into 256 sampling periods SP1', SP2', SP3', . . . , SP256' as shown by the vertical chain lines in the middle part and the lower part of FIG. 6.

The middle part of FIG. 6 shows a way of determining the unequal sampling periods SP1' to SP256'. The middle part of FIG. 6 is the same as the middle part of FIG. 5 in that it shows 0th-order moment but differs from the middle part of FIG. 5 only in the intervals between the horizontal chain lines in the drawing. In other words, the horizontal chain lines are drawn, in such a manner that the 0th-order moment rises in equal increment. The vertical chain lines are drawn so as to pass through the intersections between the horizontal chain lines and the thick line indicating the 0th-order moment.

In the first method, the sampling periods SP1' to SP256' are determined so that each time integral value of the absolute value of the magnetic field intensity of the gradient magnetic field Gro in the readout direction (whose back end of the integral interval is the representative time of each of the sampling periods SP1' to SP256') is equally spaced.

In common to all the integration periods, the start time of the integral interval for the above-described time integral value is the start time of application of the pulses of the gradient magnetic field Gro in the readout direction, for example. In addition, the above-described representative time may be the ending time or the central time of each of the sampling periods SP1' to SP256'.

According to the first method, the k-space data are generated by sampling the MR signals at unequal time intervals in the sampling periods determined as described above. The matrix elements of the k-space data generated in this way are placed at equal intervals in the k-space. The above-described expression "placed at equal intervals in the k-space" means that the values of 0th-order moment corresponding to the respective sampling periods are arranged at equal intervals as shown by the horizontal chain lines in the middle part of FIG. 6.

In other words, according to the first method, the MR signals are sampled at unequal time intervals, in such a manner that each 0th-order moment at each time of acquiring (receiving) a part of the MR signal corresponding to each sampling period becomes equally-spaced.

Figure 7:
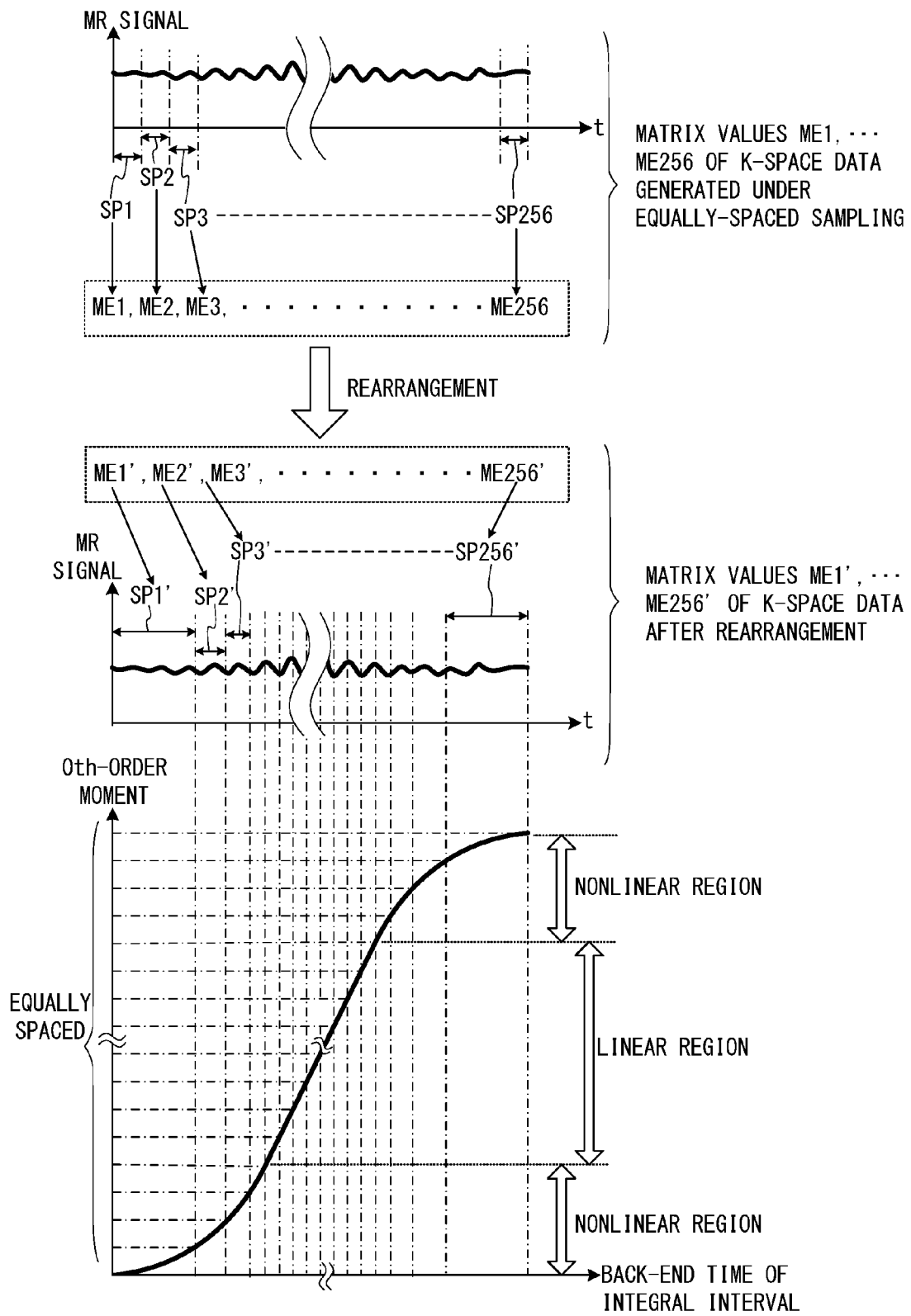
FIG. 7 is a schematic diagram showing a concept of the second method of regridding processing of the present embodiment.

FIG. 7 is a schematic diagram showing a concept of the second method of the regridding processing of the present embodiment. The upper part of FIG. 7 shows matrix values ME1, ME2, ME3, ME4, . . . , ME256 of the matrix elements for one line of the k-space data generated by sampling MR signals at equal intervals as shown in the lower part of FIG. 5.

As an example here, since it is assumed that the number of frequency encode steps is 256, the number of matrix elements for one line is also 256. The matrix values ME1, ME2, ME3, . . . , ME256 correspond to the respective sampling periods SP1, SP2, SP3, . . . , SP256 for the MR signals shown above them in the drawing.

According to the second method, k-space data are generated by sampling the MR signals at equal time intervals as shown in the upper part of FIG. 7. Afterward, the k-space data are rearranged (converted) into the new k-space data, so that each time integral value of the pulse intensity of the gradient magnetic field Gro in the readout direction up to the representative time of the sampling period corresponding to each matrix element is equally-spaced. The rearrangement can be achieved by processing such as interpolation, and the representative time is the same as that in the first method.

The middle part of FIG. 7 shows matrix values ME1', ME2', ME3', . . . , ME256' of the rearranged k-space data in the upper half and shows the original MR signals (the same MR signals as those shown in the upper part of FIG. 7) in the lower half.

The matrix values ME1', ME2', ME3', . . . , ME256' are values that must have been obtained from the signal intensity of each divided part of the original MR signal sampled in the sampling periods SP1' to SP256' (the same sampling periods as those shown in the lower part of FIG. 6).

The lower part of FIG. 7 shows the same 0th-order moment as those shown in the middle part of FIG. 6. As shown by the horizontal chain lines that equally divide the 0th-order moment in the lower part of FIG. 7, the values of 0th-order moment corresponding to the matrix elements of the rearranged k-space data are arranged at equal intervals.

In other words, according to the second method, the k-space data are rearranged, in such a manner that each 0th-order moment at each time of acquiring the part of the MR signal corresponding to each matrix element becomes equally-spaced.

Operation of the Present Embodiment

Figure 8:
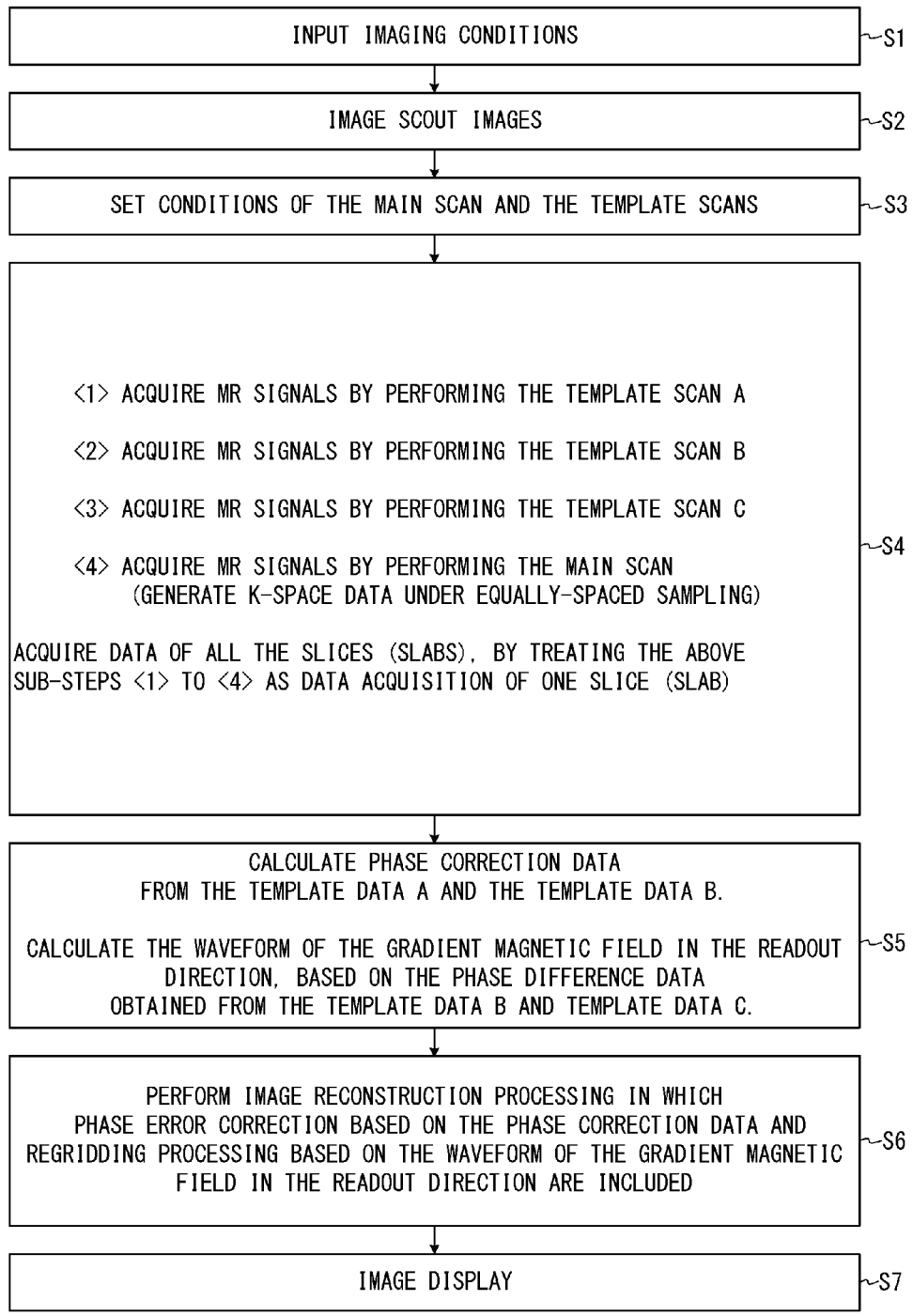
FIG. 8 is a flowchart illustrating an example of a flow of an imaging operation performed by the MRI apparatus of the present embodiment, when the second method of the regridding processing is selected.

FIG. 8 is a flowchart illustrating an example of a flow of an imaging operation performed by the MRI apparatus 10 when the second method of the regridding processing is selected. In the following, according to the step numbers in the flowchart shown in FIG. 8, an operation of the MRI apparatus 10 will be described by referring to the above-described FIG. 1 to FIG. 7 as required.

[Step S1] The system control function 61 (FIG. 1) of the processing circuitry 60 sets some of the imaging conditions of the main scan based on the imaging conditions inputted to the MRI apparatus 10 via the input device 72. As an example here, it is assumed that EPI is selected as the main scan. In addition, some conditions such as the center frequency of the RF pulse are determined by performing prescans. Moreover, the wearable type RF coil 100 is attached on the object P on the table 22 as an example.

Afterward, the processing proceeds to the Step S2.

[Step S2] The table moving structure 23 moves the table 22 under the control of the system control function 61, in such a manner that the imaging part of the object P is positioned at the magnetic field center inside the gantry 30.

Next, the system control function 61 of the processing circuitry 60 controls each component of the MRI apparatus 10 so that data of scout images are acquired. More specifically, electric currents are supplied from the shim coil power source 44 to the shim coil 32, and thereby the static magnetic field formed in the imaging space is uniformed.

Then, the system control function 61 drives the gradient coil power source 46, the RF transmitter 48, and the RF receiver 50 in accordance with the pulse sequence, and thereby gradient magnetic fields are formed in the imaging region where the object P is placed, and RF pulses are generated from the RF coil 34.

Therefore, the MR signals generated by nuclear magnetic resonance inside the object P are received by at least one of the wearable type RF coil 100, the reception RF coil 24, and the whole body coil, and the received MR signals are inputted to the RF receiver 50.

The RF receiver 50 performs the above-described predetermined signal processing on the inputted MR signals so as to generate the raw data of MR signals, and outputs these raw data to the image reconstruction function 62 of the processing circuitry 60.

The image reconstruction function 62 of the processing circuitry 60 arranges and stores the raw data of MR signals as k-space data.

The image reconstruction function 62 reconstructs image data by performing the image reconstruction processing including Fourier transformation on the k-space data, and stores the reconstructed image data in the memory circuitry 76.

The image processing function 64 of the processing circuitry 60 obtains the reconstructed image data from the memory circuitry 76 and generates two-dimensional display image data of the scout images by the performing predetermined image processing on the obtained image data. The image processing function 64 stores the display image data of the scout images in the memory circuitry 76.

Afterward, the display 74 displays the scout images indicated by the display image data of the scout images, under the control of the system control function 61 of the processing circuitry 60.

Afterward, the processing proceeds to the Step S3.

[Step S3] The system control function 61 sets the rest of the imaging conditions of the main scan including its pulse sequence, in accordance with the imaging conditions selected by a user on the basis of the displayed scout images such as FOV.

Next, the system control function 61 sets the pulse sequence of the template scan A, whose conditions are changed only in the above-described two points from the pulse sequence of the main scan (see the middle part of FIG. 2).

In addition, the system control function 61 sets the pulse sequence of the template scan B, whose conditions are changed only in the above-described two points from the pulse sequence of the template scan A (see the bottom part of FIG. 2).

Furthermore, the system control function 61 sets the pulse sequence of the template scan C whose acquisition region for the MR signals is shifted in the readout direction by the predetermined interval from the acquisition region of the template scan B (see the bottom part of FIG. 4).

Afterward, the processing proceeds to the Step S4.

[Step S4] The MRI apparatus 10 performs the template scans A, B, and C and the main scan explained with FIG. 2 and FIG. 4 in accordance with the flow composed of the following sub-steps <1> to <4>.

<1> The system control function 61 of the processing circuitry 60 causes the MRI apparatus 10 to perform the pulse sequence of the template scan A by controlling each component of the MRI apparatus 10, in the way similar to the operation of acquiring the MR signals of the scout images. Thereby, the MR signals acquired in the template scan A are sampled, and stored in the phase difference data calculating function 65 of the processing circuitry 60 as the k-space data.

<2> In a similar manner as described above, the pulse sequence of the template scan B is performed, and the MR signals acquired by the template scan B are sampled and stored in the phase difference data calculating function 65 as the k-space data.

<3> In a similar manner as described above, the pulse sequence of the template scan C is performed, and the MR signals acquired by the template scan C are sampled and stored in the phase difference data calculating function 65 as the k-space data.

Here, as to the execution of the above template scans A to C, the following two points are complemented.

Firstly, the detection frequency in the readout direction of the RF receiver 50 during the implementation term of the template scan C is shifted by Δf from the detection frequency in the readout direction during the implementation term of the template scan B. Thereby, the acquisition region of the MR signals in the template scan C is shifted by the predetermined interval (for example, five pixels to ten pixels) in the readout direction from that of the template scan B.

Secondly, in the calculation processing of the phase correction data dV(xr) for correcting the phase errors and the phase difference data Δθ(t) for the regridding processing, only the center line (i.e. the MR signal at the effective echo time) of the k-space data is used in the above-described example. Thus, it is enough to acquire up to the MR signals corresponding to the center line of the k-space data, and acquisition of the MR signals generated after the MR signal to be arranged as the center line may be omitted.

<4> In a similar manner as described above, the pulse sequence of the main scan is performed, and the MR signals acquired by the main scan are sampled and stored in the image reconstruction function 62 of the processing circuitry 60 as the k-space data.

The MRI apparatus 10 performs data acquisition of all the slices (slabs), by treating the processing of the sub-steps <1> to <4> as data acquisition of one slice (or one slab).

Incidentally, as an example in the acquisition of the respective MR signals of the above sub-steps <1> to <4>, the k-space data are once generated by sampling the MR signals at equal time intervals.

In addition, the order of the above sub-steps <1> to <4> is only an example and the order may be changed.

Afterward, the processing proceeds to the Step S5.

[Step S5] The phase difference data calculating function 65 of the processing circuitry 60 calculates the phase correction data dV(xr) for correcting the phase error for every slice (or every slab), based on the template data A and B stored in the image reconstruction function 62 and the above-described formula (3). The phase difference data calculating function 65 outputs the phase correction data dV(xr) to the image reconstruction function 62.

In addition, the phase difference data calculating function 65 calculates the phase difference data Δθ(t) in the readout direction for the regridding processing for every slice (or every slab), based on the template data B and C stored in the image reconstruction function 62 and the above-described formulas (5) to (12).

The image reconstruction function 62 of the processing circuitry 60 acquires the phase difference data Δθ(t) from the phase difference data calculating function 65, and calculates (reproduces) the waveform of the gradient magnetic field Gro in the readout direction at the time of performing the main scan, based on the phase difference data Δθ(t).

Afterward, the processing proceeds to the Step S6.

[Step S6] The image reconstruction function 62 performs the regridding processing of the above-described second method (see FIG. 7) on the k-space data of each slice (or each slab) of the main scan generated by sampling the MR signals at equal time intervals in the Step S5.

In other words, the k-space data are rearranged so that each time integral value of the magnetic field intensity of the gradient magnetic field Gro in the readout direction (whose back end of the integral interval is the representative time of each of the sampling periods) becomes equally spaced. Thereby, the k-space data subjected to the regridding processing are generated.

The image reconstruction function 62 performs the image reconstruction processing including the correction processing of phase errors on the k-space data subjected to the regridding processing, based on the above-described phase correction data dV(xr) (this processing is performed for each slice or slab, and Fourier transformation is included in the image reconstruction processing).

Thereby, the image data of the main scan in which phase errors have been corrected are reconstructed for each slice (or each slab). The image reconstruction function 62 stores the reconstructed image data of the main scan in the memory circuitry 76.

The image processing function 64 of the processing circuitry 60 takes in the reconstructed image data from the memory circuitry 76, generates two-dimensional display image data by performing predetermined processing on the reconstructed image data, and stores the display image data in the memory circuitry 76.

Afterward, the processing proceeds to the Step S7.

[Step S7] The system control function 61 causes the display 74 to display images indicated by the display image data.

The above is the explanation of the flow of FIG. 8.

Figure 9:
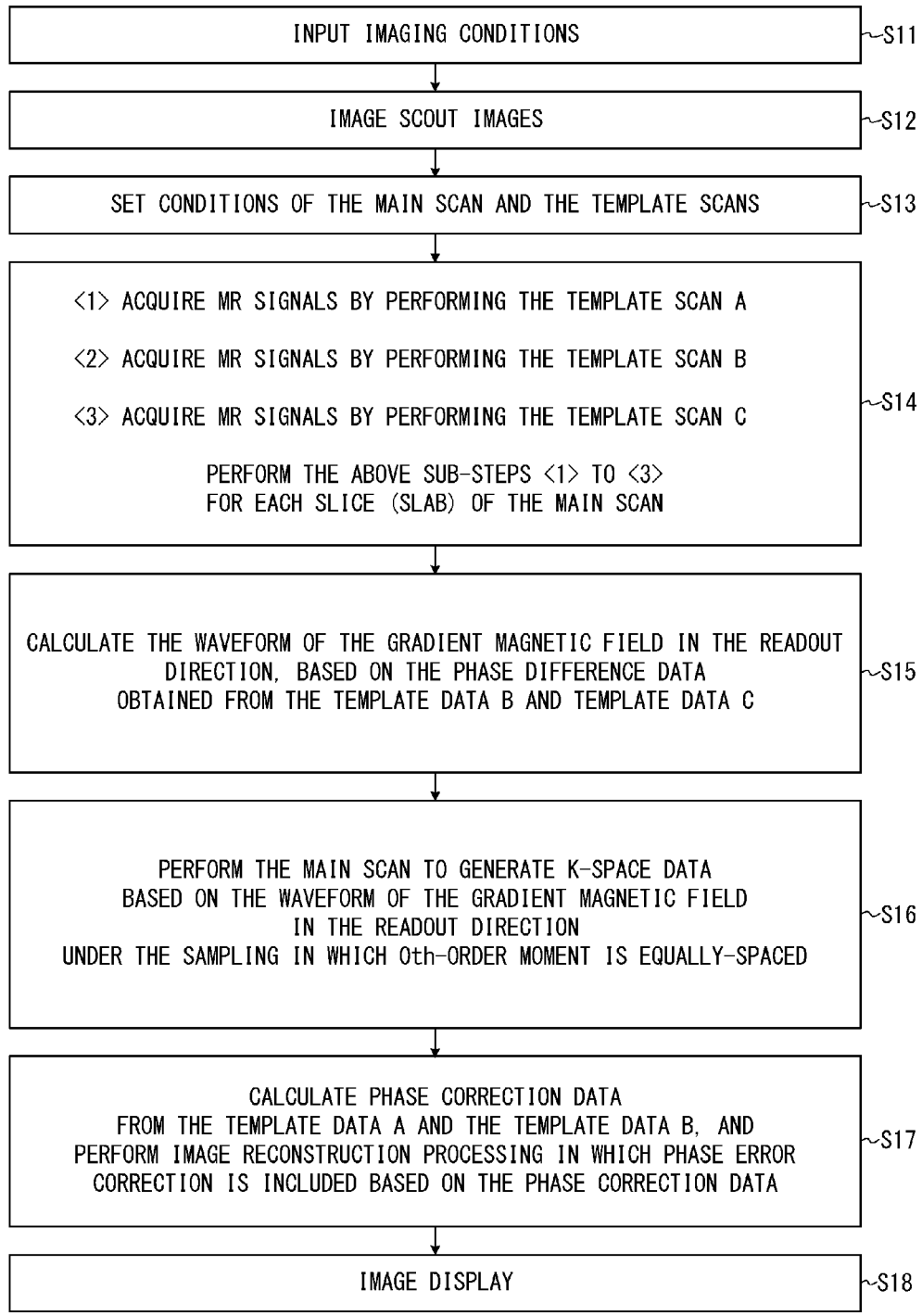
FIG. 9 is a flowchart illustrating an example of a flow of an imaging operation performed by the MRI apparatus of the present embodiment, when the first method of the regridding processing is selected.

FIG. 9 is a flowchart illustrating an example of a flow of an imaging operation performed by the MRI apparatus 10 when the first method of the regridding processing is selected. In the following, according to the step numbers in the flowchart shown in FIG. 9, an operation of the MRI apparatus 10 will be described by referring to the above-described FIG. 1 to FIG. 8 as required.

[Steps S11 to S13] The processing of the Steps S11 to S13 is the same as the processing of the Steps S1 to S3 in FIG. 8.

Afterward, the processing proceeds to the Step S14.

[Step S14] The MRI apparatus 10 performs the template scans A, B and C on the respective slices (or slab), and the template data A, B and C are stored in the phase difference data calculating function 65 of the processing circuitry 60 as the k-space data. The processing of the Step S14 is the same as the Step S4 in FIG. 8, except that the pulse sequence of the main scan is not performed.

Afterward, the processing proceeds to the Step S15.

[Step S15] In a way similar to the Step S5 in FIG. 8, the phase difference data calculating function 65 of the processing circuitry 60 calculates the phase difference data $\Delta\theta(t)$ in the readout direction for the regridding processing, and outputs the phase difference data $\Delta\theta(t)$ to the image reconstruction function 62 of the processing circuitry 60.

In a similar manner as described above, the image reconstruction function 62 calculates the waveform of the gradient magnetic field Gro in the readout direction at the time of performing the main scan, based on the phase difference data $\Delta\theta(t)$.

Afterward, the processing proceeds to the Step S16.

[Step S16] The MRI apparatus 10 performs the pulse sequence of the main scan for the respective slices (or slabs), generates the k-space data by sampling the acquired MR signals, and stores the k-space data in the image reconstruction function 62 of the processing circuitry 60.

At this time, the image reconstruction function 62 generates the k-space data by sampling the MR signals at unequal time intervals under the above-described first method (see FIG. 6), based on the waveform of the gradient magnetic field Gro in the readout direction calculated in the Step S15.

In other words, each line of the acquired MR signals is sampled at unequal time intervals so that 0th-order moment of the gradient magnetic field Gro in the readout direction becomes equally spaced. In this way, the k-space data which have been subjected to the regridding processing are generated.

Afterward, the processing proceeds to the Step S17.

[Step S17] In the same way as the Step S5 in FIG. 8, the phase difference data calculating function 65 of the processing circuitry 60 calculates the phase correction data dV(xr) for correcting phase errors, and outputs the phase correction data dV(xr) to the image reconstruction function 62.

In the same way as the Step S6 in FIG. 8, the image reconstruction function 62 performs the image reconstruction processing including the correction of phase errors based on the phase correction data dV(xr), on the k-space data which are subjected to the regridding processing and generated in the Step S16. The image reconstruction function 62 stores the image data of the main scan reconstructed in this manner in the memory circuitry 76.

The image processing function 64 of the processing circuitry 60 generates two-dimensional display image data (of the main scan images) by performing the predetermined image processing on the above reconstructed image data, and stores the generated display image data in the memory circuitry 76

Afterward, the processing proceeds to the Step S18.

[Step S18] The display 74 displays the images indicated by the display image data (of the main scan images), under the control of the system control function 61 of the processing circuitry 60.

The foregoing is a description of operations of the MRI apparatus 10 according to the present embodiment.

Effects of the Present Embodiment

The conceptual explanation of the principle of the regridding processing of the present embodiment is as follows.

Consider a case where the detection frequency in the readout direction is shifted by $\Delta f$ in a period from sampling time tx to sampling time ty during which intensity of the gradient magnetic field Gro in the readout direction is constant. In this case, the phase of the readout direction in each sampling time is shifted at equal intervals, and positional information of the readout direction added to the MR signal at each sampling time is shifted at equal intervals. In such an ideal case, the regridding processing is unnecessary.

However, the actual waveform of the gradient magnetic field Gro in the readout direction is not a rectangular wave, and ramp sampling is sometimes performed in the rising period and the falling period. Moreover, the actual waveform of the gradient magnetic field Gro in the readout direction includes an overshoot, an undershoot, and so on.

If the detection frequency in the readout direction is shifted by $\Delta f$ in the period during which intensity of the gradient magnetic field Gro in the readout direction is changing, the phase of the readout direction at each sampling time becomes equal to the product of $\Delta f$ and intensity of the gradient magnetic field Gro in the readout direction at each sampling time. In this case, the phase of the readout direction at each sampling time is shifted at unequal intervals.

Here, as to reproducing a waveform, to use only the template data B does not enable reproduction of the waveform of the gradient magnetic field Gro in the readout direction in the period during which the acquired MR signals are detected by at least one of the whole body coil, the reception RF coil 24, and the wearable type RF coil 100. However, the phase difference data $\Delta\theta(t)$ in the readout direction can be calculated by appropriately using the respective k-space data of the template scans B and C whose detection frequencies in the readout direction are different from each other by $\Delta f$. This is because influence on the phase due to non-uniformity of the magnetic field can be canceled by the difference between the template data B and C.

In the present embodiment, the waveform of the gradient magnetic field Gro in the readout direction is precisely reproduced by the phase difference data $\Delta\theta(t)$ in the readout direction, and the regridding processing is performed based on the gradient magnetic field Gro in the readout direction precisely calculated in this way. As a result, accuracy of the regridding processing can be improved.

In addition, the present embodiment is not a technique in which the gradient magnetic field Gro in the readout direction is calculated based on (a) measurement of a search coil and an integrator, (b) simulation, or (c) measurement using MR signals. In the present embodiment, since the gradient magnetic field Gro in the readout direction is calculated from the respective k-space data of the two template scans B and C whose acquisition regions for the MR signals are spatially shifted from each other in the readout direction, time for measurement is not required and the regridding processing can be performed easily and accurately.

In addition, when two template scans are performed for correcting phase errors and further two template scans are performed for the regridding processing, the number of the template scans becomes four and the imaging time becomes longer. In the present embodiment, the template scan B is also used for correcting the phase errors together with the template scan A. Since the number of the template scans is only three, satisfactory images can be obtained without prolonging imaging time.

According to the above-described embodiment, the regridding processing in MRI can be performed more precisely than conventional technology.

Supplementary Notes on the Present Embodiment

[1] In the above-described embodiment, an example in which the phase difference data $\Delta\theta(t)$ in the readout direction are calculated from the center lines of the respective k-space data of the template scans B and C and the regridding processing is performed based on these phase difference data $\Delta\theta(t)$ has been explained.

This is based on the premise that distortion of the waveform of the gradient magnetic field Gro in the readout direction at the time of detecting the MR signal arranged at the center line of a k-space is the same as distortion of the waveform of the gradient magnetic field Gro in the readout direction at the time of detecting each MR signal arranged at each line of the end side of the k-space. However, embodiments of the present invention are not limited to such an aspect.

For example, consider a case where performance of devices such as a non-illustrated gradient magnetic field amplifier inside the gradient coil power source 46 is not satisfactory. In this case, the waveform of the gradient magnetic field Gro in the readout direction of the main scan is sometimes different between an echo (MR signal) detected at earlier time and an echo detected at the time close to end.

As described above, when the waveform of the gradient magnetic field Gro in the readout direction at the time of detecting an echo (MR signal) corresponding to each line of the k-space is different for each line of the k-space, the regridding processing may be performed in the following manner.

Specifically, the regridding processing on the k-space data acquired for reconstructing one image can be performed for each line of these k-space data, as explained in FIG. 6 and FIG. 7. In other words, in the case of the k-space data whose phase encode step number and frequency encode step number are both 256, the regridding processing can be performed for each of the 256 lines.

Accordingly, for example, the phase difference data $\Delta\theta(t)$ in the readout direction are calculated for each line of the k-space by using all the MR signals acquired in the template scans B and C in FIG. 4. Then, the regridding processing (FIG. 6 and FIG. 7) is performed for each line of the k-space based on the phase difference data $\Delta\theta(t)$ calculated for each line.

More specifically, for example, the phase difference data $\Delta\theta_{k=-3}(t)$ of the line of K=−3 (this line corresponds to the phase encode step −3, if the gradient magnetic field Gpe in the phase encode direction is applied) are calculated for the corresponding MR signals acquired in the beginning part of the template scans B and C. The regridding processing onto the line of K=−3 of the k-space data can be performed on the basis of these phase difference data $\Delta\theta_{k=-3}(t)$.

Similarly, the phase difference data $\Delta\theta_{k=-2}(t)$ of the line of K=−2 are calculated for the MR signals secondly acquired in the respective template scans B and C, and the regridding processing onto the line of K=−2 of the k-space data can be performed based on these phase difference data $\Delta\theta_{k=-2}(t)$.

After this, the processing similar to the above is repeated from the line of k=−1 to the finally detected line.

[2] As an example of processing order in the above-described embodiment, the template scans A, B and C and the main scan are performed, then the phase correction data for the phase error correction and the phase difference data for the regridding processing are calculated, and then the image reconstruction processing including the phase error correction and the regridding processing is performed. However, this is only an example of order for simplifying the explanation.

Calculation of the phase correction data for the phase error correction, calculation of the phase difference data for the regridding processing, and the image reconstruction processing including the phase error correction and the regridding processing may be performed in parallel with execution of the template scans A to C and the main scan for other slices, after completion of the template scans A to C and the main scan for one slice.

[3] In the above-described embodiment, an example in which the phase difference data for the regridding processing are calculated by performing two template scans B and C has been explained. However, embodiments of the present invention are not limited to such an aspect.

The phase difference data for the regridding processing may be calculated by performing three template scans whose acquisition regions of the MR signals are shifted from each other in the readout direction. Additionally, the phase difference data for the regridding processing may be calculated by performing four or more template scans.

For example, consider a case where template scans B, C, D, E, F, G, and H are performed and the acquisition region of the MR signals of the template scan B is the reference. Then, each shift amount by which the acquisition region of the MR signals of each of the template scans C, D, E, F, G and H is shifted from that of the template scan B may be determined to five pixels, six pixels, seven pixels, eight pixels, nine pixels, and ten pixels in order.

In this case, the phase difference data for the regridding processing is finally determined by taking the average of the six sets of data: the first phase difference data calculated from the template data B and C, the second phase difference data calculated from the template data B and D, the third phase difference data calculated from the template data B and E, the fourth phase difference data calculated from the template data B and F, the fifth phase difference data calculated from the template data B and G, and the sixth phase difference data calculated from the template data B and H.

[4] In the above-described embodiment, an example in which the phase error correction is performed by executing the template scan A has been explained. However, embodiments of the present invention are not limited to such an aspect.

When the phase error is not so large, the sequence is set so as not to perform the calculation of the phase correction data (phase error correction) by omitting the template scan A. In this case, since the number of the template scans is reduced to two, scan time can be further shortened and power consumption can be further reduced.

[5] An example, in which (a) the MR signal at the effective echo time is an odd number-th echo in each of the main scan and the template scan A and (b) the polarity of the gradient magnetic field Gro in the readout direction at the effective echo time is negative in each of the main scan and the template scan A, has been explained in the above-described embodiment.

In this case, for the above-described reasons, it is preferable that the MR signal at the effective echo time is an even number-th echo and the polarity of the gradient magnetic field Gro in the readout direction at the effective echo time is positive in each of the template scans B and C. However, embodiments of the present invention are not limited to such an aspect.

In each of the main scan and the template scan A, the MR signal at the effective echo time may be an odd number-th echo and the polarity of the gradient magnetic field Gro in the readout direction at the effective echo time may be positive. In this case, each of the template scans B and C is preferably configured so that the MR signal at the effective echo time is an even number-th echo and the polarity of the gradient magnetic field Gro in the readout direction at the effective echo time is negative.

Additionally, in the main scan and the template scan A, the MR signal at the effective echo time may be an even number-th echo and the polarity of the gradient magnetic field Gro in the readout direction at the effective echo time may be negative. In this case, each of the template scans B and C is preferably configured so that the MR signal at the effective echo time is an odd number-th echo and the polarity of the gradient magnetic field Gro in the readout direction at the effective echo time is positive.

Additionally, in the main scan and the template scan A, the MR signal at the effective echo time may be an even number-th echo and the polarity of the gradient magnetic field Gro in the readout direction at the effective echo time may be positive. In this case, each of the template scans B and C is preferably configured so that the MR signal at the effective echo time is an odd number-th echo and the polarity of the gradient magnetic field Gro in the readout direction at the effective echo time is negative.

[6] If a period of acquiring MR signals is shortened, it sometimes causes a case where the waveform of the gradient magnetic field Gro in the readout direction cannot be regarded as constant compared with a sampling interval at the time of generating the k-space data. In this case, it is preferable that the raw data of the sampled MR signals are rearranged at equal intervals in the k-space by performing the regridding processing prior to the image reconstruction processing.

Thus, not only in the pulse sequence of EPI but also in case where a waveform includes an overshoot or an undershoot, image quality can be improved by precisely calculating the waveform of the gradient magnetic field in the readout direction of the main scan under the method of the above-described embodiment and performing the regridding processing based on the calculated waveform of the gradient magnetic field.

In other words, the technique of the above-described embodiment is applicable to any pulse sequence including a period during which magnetic field intensity is non-constant in the waveform of the gradient magnetic field Gro in the readout direction while detecting MR signals, and accuracy of the regridding processing can be improved by applying the technique of the above-described embodiment.

[7] Correspondences between terms used in the claims and terms used in the embodiment described above will be described.

Note that the correspondences described below are just some of possible interpretations for reference and should not be construed as limiting embodiments of the present invention.

The X axis gradient coil $33x$, the Y axis gradient coil $33y$, and the Z axis gradient coil $33z$ are examples of the gradient coil described in the claims.

The wearable type RF coil 100 receiving MR signals, the reception RF coil 24 receiving MR signals, and the RF coil 34 (the whole body coil as an example in the above-described embodiment) which transmits RF pulses and receives MR signals are examples of the RF coil described in the claims.

The RF transmitter 50 is an example of the RF transmitter described in the claims.

The processing circuitry 60 is an example of the processing circuitry described in the claims.

The template scan B is an example of the first pulse sequence described in the claims.

The template scan C is an example of the second pulse sequence described in the claims.

The template scan A is an example of the third pulse sequence described in the claims.

[8] The term processor used in the above explanation regarding the processing circuitry 60 means, for instance, a circuit such as a CPU (Central Processing Unit), a GPU (Graphics Processing Unit), an ASIC (Application Specific Integrated Circuit), a programmable logic device including an SPLD (Simple Programmable Logic Device) and a CPLD (Complex Programmable Logic Device) as examples, an FPGA (Field Programmable Gate Array), and so on.

The number of processors provided in the processing circuitry 60 may be one, two, or more than two.

Each processor included in the processing circuitry 60 implements each function by reading out a program directly stored in its own circuit and executing the program. Additionally or alternatively, the programs may be stored in non-illustrated memories provided in the processing circuitry 60, instead of storing those programs in the processors.

[9] While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
a gradient coil configured to apply a gradient magnetic field in accordance with a pulse sequence;
an RF coil configured to transmit RF pulses causing nuclear magnetic resonance and receive nuclear magnetic resonance signals in accordance with the pulse sequence;
an RF receiver configured to acquire the nuclear magnetic resonance signals received by the RF coil in accordance with the pulse sequence; and
processing circuitry configured to control the gradient coil, the RF coil, and the RF receiver to perform a first pulse sequence, a second pulse sequence, and a main-scan pulse sequence,
wherein the processing circuitry is configured to
(a) set the first pulse sequence in which application of a gradient magnetic field in a readout direction is included, in such a manner that the nuclear magnetic resonance signals are acquired from a first acquisition region including at least a part of an imaging region of a main scan,
(b) set the second pulse sequence in which application of the gradient magnetic field in the readout direction is included, in such a manner that the nuclear magnetic resonance signals are acquired from a second acquisition region including at least a part of the imaging region and being shifted from the first acquisition region,
(c) set the main-scan pulse sequence in which application of the gradient magnetic field in the readout direction and a gradient magnetic field in a phase encode direction is included, in such a manner that the nuclear magnetic resonance signals from the imaging region are acquired,
(d) generate first k-space data including a plurality of matrix elements, by sampling the nuclear magnetic resonance signals acquired by the first pulse sequence,
(e) generate second k-space data including a plurality of matrix elements, by sampling the nuclear magnetic resonance signals acquired by the second pulse sequence,
(f) calculate phase difference data indicative of phase difference in the readout direction between the first k-space data and the second k-space data,
(g) generate main scan k-space data based on the nuclear magnetic resonance signals acquired by the main-scan pulse sequence and the phase difference data, and
(h) reconstruct image data of the imaging region based on the main scan k-space data.

2. The magnetic resonance imaging apparatus according to claim 1,
wherein the processing circuitry is configured to
(a) calculate the phase difference data as a function of elapsed time when the gradient magnetic field in the readout direction is applied,
(b) calculate a waveform of the gradient magnetic field in the readout direction based on the phase difference data,
(c) generate the main-scan k-space data based on the nuclear magnetic resonance signals acquired by the main-scan pulse sequence and the waveform of the gradient magnetic field in the readout direction, so that each time integral value up to each sampling period corresponding to each of the matrix elements is equally-spaced, and
(d) reconstruct the image data by performing image reconstruction processing including Fourier transformation on the main-scan k-space data.

3. The magnetic resonance imaging apparatus according to claim 2,
wherein the processing circuitry is configured to calculate the phase difference data based on (a) data corresponding to a nuclear magnetic resonance signal acquired at a timing of effective echo time of the first k-space data and (b) data corresponding to a nuclear magnetic resonance signal acquired at a timing of effective echo time of the second k-space data.

4. The magnetic resonance imaging apparatus according to claim 3,
wherein the processing circuitry is configured to
(a) set the first pulse sequence to acquire the nuclear magnetic resonance signals by repeating inversion of polarity of the gradient magnetic field in the readout direction,
(b) set the second pulse sequence to acquire the nuclear magnetic resonance signals by repeating inversion of polarity of the gradient magnetic field in the readout direction, and
(c) set a pulse sequence of echo planar imaging in which inversion of polarity of the gradient magnetic field in the readout direction is repeated, as the main-scan pulse sequence.

5. The magnetic resonance imaging apparatus according to claim 4,
wherein the processing circuitry is configured to shift the second acquisition region from the first acquisition region, by shifting a detection frequency of the RF receiver in the second pulse sequence from a detection frequency of the RF receiver in the first pulse sequence.

6. The magnetic resonance imaging apparatus according to claim 5,
wherein the processing circuitry is configured to
(a) set the first pulse sequence to acquire the nuclear magnetic resonance signals from an acquisition region which is expanded in the readout direction from an acquisition region of the nuclear magnetic resonance signals of the main-scan pulse sequence, and
(b) set the second pulse sequence to acquire the nuclear magnetic resonance signals from an acquisition region which is expanded in the readout direction from the acquisition region of the nuclear magnetic resonance signals of the main-scan pulse sequence.

7. The magnetic resonance imaging apparatus according to claim 6,
wherein the processing circuitry is configured to
(a) set a third pulse sequence in which application of the gradient magnetic field in the readout direction is included, in such a manner that the nuclear magnetic resonance signals are acquired from a third acquisition region including at least a part of the imaging region,
(b) set each of the first pulse sequence and the second pulse sequence in such a manner that polarity of the gradient magnetic field in the readout direction at effective echo time becomes opposite to polarity of the gradient magnetic field in the readout direction at effective echo time of the third pulse sequence,
(c) control the gradient coil, the RF coil, and the RF receiver to perform the third pulse sequence in addition to the first pulse sequence, the second pulse sequence, and the main-scan pulse sequence, (d) generate third k-space data including a plurality of matrix elements, by sampling the nuclear magnetic resonance signals acquired by the third pulse sequence, and (e) reconstruct the image data by correcting phase error included in the nuclear magnetic resonance signals acquired by the main-scan pulse sequence, based on phase correction data obtained from the first k-space data and the third k-space data.

8. The magnetic resonance imaging apparatus according to claim 4, wherein the processing circuitry is configured to (a) set unequally-spaced sampling periods, so that each time integral value, whose back end of integral interval is a representative time of each of sampling periods for the nuclear magnetic resonance signals, is equally-spaced, and (b) generate the main-scan k-space data by sampling the nuclear magnetic resonance signals acquired by the main-scan pulse sequence based on the unequally-spaced sampling periods.

9. The magnetic resonance imaging apparatus according to claim 4, wherein the processing circuitry is configured to (a) generate the main-scan k-space data by sampling the nuclear magnetic resonance signals acquired by the main-scan pulse sequence at equally-spaced intervals, (b) perform rearrangement on the main-scan k-space data so that each time integral value whose back end of integral interval is a representative time of each sampling period corresponding to each matrix element of the main-scan k-space data is placed at equal intervals, and (c) reconstruct the image data by performing image reconstruction processing including Fourier transformation on the main-scan k-space data subjected to the rearrangement.

10. The magnetic resonance imaging apparatus according to claim 3, wherein the processing circuitry is configured to shift the second acquisition region from the first acquisition region, by shifting a detection frequency of the RF receiver in the second pulse sequence from a detection frequency of the RF receiver in the first pulse sequence.

11. The magnetic resonance imaging apparatus according to claim 3, wherein the processing circuitry is configured to (a) set the first pulse sequence to acquire the nuclear magnetic resonance signals from an acquisition region which is expanded in the readout direction from an acquisition region of the nuclear magnetic resonance signals of the main-scan pulse sequence, and (b) set the second pulse sequence to acquire the nuclear magnetic resonance signals from an acquisition region which is expanded in the readout direction from the acquisition region of the nuclear magnetic resonance signals of the main-scan pulse sequence.

12. The magnetic resonance imaging apparatus according to claim 3, wherein the processing circuitry is configured to (a) set a third pulse sequence in which application of the gradient magnetic field in the readout direction is included, in such a manner that the nuclear magnetic resonance signals are acquired from a third acquisition region including at least a part of the imaging region, (b) set each of the first pulse sequence and the second pulse sequence in such a manner that polarity of the gradient magnetic field in the readout direction at effective echo time becomes opposite to polarity of the gradient magnetic field in the readout direction at effective echo time of the third pulse sequence, (c) control the gradient coil, the RF coil, and the RF receiver to perform the third pulse sequence in addition to the first pulse sequence, the second pulse sequence, and the main-scan pulse sequence, (d) generate third k-space data including a plurality of matrix elements, by sampling the nuclear magnetic resonance signals acquired by the third pulse sequence, and (e) reconstruct the image data by correcting phase error included in the nuclear magnetic resonance signals acquired by the main-scan pulse sequence, based on phase correction data obtained from the first k-space data and the third k-space data.

13. The magnetic resonance imaging apparatus according to claim 2, wherein the processing circuitry is configured to (a) set unequally-spaced sampling periods, so that each time integral value, whose back end of integral interval is a representative time of each of sampling periods for the nuclear magnetic resonance signals, is equally-spaced, and (b) generate the main-scan k-space data by sampling the nuclear magnetic resonance signals acquired by the main-scan pulse sequence based on the unequally-spaced sampling periods.

14. The magnetic resonance imaging apparatus according to claim 2, wherein the processing circuitry is configured to (a) generate the main-scan k-space data by sampling the nuclear magnetic resonance signals acquired by the main-scan pulse sequence at equally-spaced intervals, (b) perform rearrangement on the main-scan k-space data, so that each time integral value whose back end of integral interval is a representative time of each sampling period corresponding to each matrix element of the main-scan k-space data is placed at equal intervals, and (c) reconstruct the image data by performing image reconstruction processing including Fourier transformation on the main-scan k-space data subjected to the rearrangement.

15. The magnetic resonance imaging apparatus according to claim 2, wherein the processing circuitry is configured to shift the second acquisition region from the first acquisition region, by shifting a detection frequency of the RF receiver in the second pulse sequence from a detection frequency of the RF receiver in the first pulse sequence.

16. The magnetic resonance imaging apparatus according to claim 2, wherein the processing circuitry is configured to (a) set the first pulse sequence to acquire the nuclear magnetic resonance signals from an acquisition region which is expanded in the readout direction from an acquisition region of the nuclear magnetic resonance signals of the main-scan pulse sequence, and (b) set the second pulse sequence to acquire the nuclear magnetic resonance signals from an acquisition region which is expanded in the readout direction from the acquisition region of the nuclear magnetic resonance signals of the main-scan pulse sequence.

17. The magnetic resonance imaging apparatus according to claim 2, wherein the processing circuitry is configured to
(a) set a third pulse sequence in which application of the gradient magnetic field in the readout direction is included, in such a manner that the nuclear magnetic resonance signals are acquired from a third acquisition region including at least a part of the imaging region,
(b) set each of the first pulse sequence and the second pulse sequence in such a manner that polarity of the gradient magnetic field in the readout direction at effective echo time becomes opposite to polarity of the gradient magnetic field in the readout direction at effective echo time of the third pulse sequence,
(c) control the gradient coil, the RF coil, and the RF receiver to perform the third pulse sequence in addition to the first pulse sequence, the second pulse sequence, and the main-scan pulse sequence,
(d) generate third k-space data including a plurality of matrix elements, by sampling the nuclear magnetic resonance signals acquired by the third pulse sequence, and
(e) reconstruct the image data by correcting phase error included in the nuclear magnetic resonance signals acquired by the main-scan pulse sequence, based on phase correction data obtained from the first k-space data and the third k-space data.

18. The magnetic resonance imaging apparatus according to claim 17,
wherein the processing circuitry is configured to
(a) set the third pulse sequence in such a manner that start timing of applying the gradient magnetic field in the readout direction, effective echo time, and polarity of the gradient magnetic field in the readout direction at the effective echo time with reference to application timing of an excitation pulse become equivalent to the main-scan pulse sequence,
(b) set each of the first pulse sequence and the second pulse sequence in such a manner that a nuclear magnetic resonance signal at the effective echo time becomes an even-numbered echo, when a nuclear magnetic resonance signal at the effective echo time in the third pulse sequence becomes an odd-numbered echo, and
(c) set each of the first pulse sequence and the second pulse sequence in such a manner that a nuclear magnetic resonance signal at the effective echo time becomes an odd-numbered echo, when a nuclear magnetic resonance signal at the effective echo time in the third pulse sequence becomes an even-numbered echo.

* * * * *